United States Patent
Killary et al.

(10) Patent No.: US 11,693,007 B2
(45) Date of Patent: Jul. 4, 2023

(54) ASSAY FOR DETECTION OF EARLY STAGE PANCREATIC CANCER

(71) Applicant: Board of Regents, The University of Texas System, Austin, TX (US)

(72) Inventors: Ann McNeill Killary, Houston, TX (US); Steven T. Lott, Houston, TX (US); Nanyue Chen, Houston, TX (US); Seetharaman Balasenthil, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 598 days.

(21) Appl. No.: 16/488,083

(22) PCT Filed: Feb. 23, 2018

(86) PCT No.: PCT/US2018/019548
§ 371 (c)(1),
(2) Date: Aug. 22, 2019

(87) PCT Pub. No.: WO2018/156973
PCT Pub. Date: Aug. 30, 2018

(65) Prior Publication Data
US 2019/0376976 A1 Dec. 12, 2019

Related U.S. Application Data

(60) Provisional application No. 62/463,348, filed on Feb. 24, 2017.

(51) Int. Cl.
*G01N 33/574* (2006.01)
(52) U.S. Cl.
CPC .............................. *G01N 33/57438* (2013.01)
(58) Field of Classification Search
CPC ................................................ G01N 33/57438
See application file for complete search history.

(56) References Cited

U.S. PATENT DOCUMENTS

| | | |
|---|---|---|
| 8,541,170 B2 | 9/2013 | Kennedy et al. |
| 2012/0040861 A1 | 2/2012 | Williams et al. |
| 2015/0315289 A1 | 11/2015 | Liu et al. |

FOREIGN PATENT DOCUMENTS

| | | | |
|---|---|---|---|
| JP | 2007212438 A | * | 8/2007 |
| WO | WO 2012-112443 | | 8/2012 |
| WO | WO 2016-049045 | | 3/2016 |

OTHER PUBLICATIONS

Thermo Fisher Scientific Inc. Tech Tip #65 :1-14, (2010).*
Balasenthil et al., "A Migration Signature and Plasma Biomarker Panel for Pancreatic Adenocarcinoma," *Cancer Prev Res* (Phila)., 4(1):137-149, 2011.
Chu et al., "Identification and Screening of Individuals at Increased Risk for Pancreatic Cancer with Emphasis on Known Environmental and Genetic Factors and Hereditary Syndromes," *JOP*, 11(3):203-212, 2010.
Evans et al., "Circulating tenascin C levels distinguish pancreatic cancer from chronic pancreatitis and correlate with pancreatic stromal expression," *Pancreatology*, 16(3):S30-S31, 2016.
Franklin et al., "Combining conventional and stroma-derived tumour markers in pancreatic ductal adenocarcinoma," *Cancer Biomarkers*, 15:1-10, 2015.
Haab et al., "Definitive Characterization of CA 19-9 in Resectable Pancreatic Cancer Using a Reference Set of Serum and Plasma Specimens," *PLoS One*, 10(10):e0139049, 2015.
Ishiwata et al., "Serum tenascin-C as a potential predictive marker of angiogenesis in non-small cell lung cancer," *Anticancer Research*, 25:489-495, 2005.
Karabulut et al., "Is serum tenascin-c level potential biomarkers in pancreatic adenocarcinoma?" *Bakirköy Tip Dergisi, Medical Journal of Bakirköy*, 12(2):76-82, 2016. (English Abstract p. 1).
Killary, "Pancreatic reference set application," Early Detection Research Network, National Cancer Institute, 2012.
Mirus et al., "Cross-Species Antibody Microarray Interrogation Identifies a 3-Protein Panel of Plasma Biomarkers for Early Diagnosis of Pancreas Cancer," *Clin Cancer Res*, 21(7):1764-1771, 2015.
Paron et al., "Tenascin-C Enhances Pancreatic Cancer Cell Growth and Motility and Affects Cell Adhesion through Activation of the Integrin Pathway," *PLoS One*, 6(6):e21684, 2011.
PCT International Search Report and Written Opinion issued in International Application PCT/2018/019548, dated May 18, 2018.
Takeda et al., "Clinical Significance of Large Tenascin-C Spliced Variant as a Potential Biomarker for Colorectal Cancer," *World J. Surg.*, 31(2):388-394, 2007.
Wu et al., "CA 19-9 and Pancreatic Cancer," *Clin Adv Hematol Oncol.*, 11(1):53-55, 2013.
Yabushita et al., "Metabolomic and transcriptomic profiling of human K-ras oncogene transgenic rats with pancreatic ductal adenocarcinomas," *Carcinogenesis*, 34(6):1251-1259, 2013.
Yoshida et al., "Tenascin-C and integrins in cancer," *Cell Adhesion & Migration*, 9(1-2):96-104; 2015.
Balasenthil et al., "A plasma biomarker panel to identify surgically resectable early-stage pancreatic cancer," *Journal of the National Cancer Institute*, 109(8):djw341, 2017.
Extended European Search Report and Search Opinion issued in European Application No. 18757880.2, dated Dec. 9, 2020.
Giblin et al., "Tenascin-C: form versus function," *Cell Adhesion and Migration*, 9(1-2):48-82, 2014.

(Continued)

*Primary Examiner* — Alana Harris Dent
(74) *Attorney, Agent, or Firm* — Parker Highlander PLLC

(57) ABSTRACT

Provided herein are methods of detecting pancreatic cancer, particularly early stage pancreatic cancer, comprising measuring the expression of the biomarker panel TNC-FN III-C, TFPI, and CA19-9. The expression may be determined by an ELISA, such as a multiplex ELISA. Further provided herein are methods of treating subjects identified to have pancreatic cancer.

15 Claims, 6 Drawing Sheets

(56) References Cited

OTHER PUBLICATIONS

Carnemolla et al., "Identification of a glioblastoma-associated tenascin-C isoform by a high affinity recombinant antibody," *American Journal of Pathology*, 154(5):1345-1352, 1999.

Gong et al., "Gemcitabine resistance induced by interaction between alternatively spliced segment of tenascin-C and annexin A2 in pancreatic cancer cells," *Biol Pharm Bull.*, 33(8):1261-1267, 2010.

Office Action issued in Japanese Application No. 2019-546156, dated Feb. 8, 2022, and English translation.

\* cited by examiner

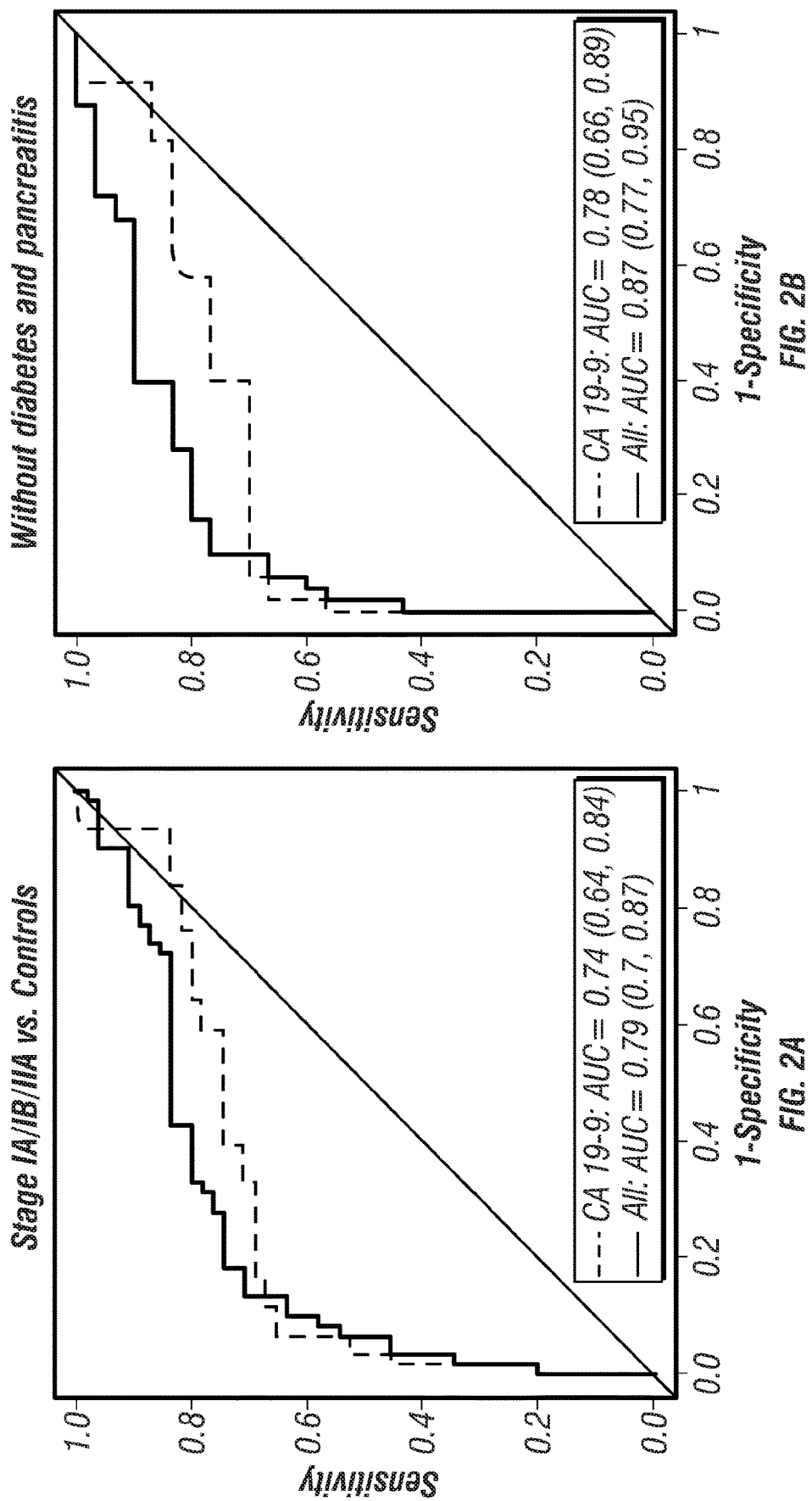

US 11,693,007 B2

ASSAY FOR DETECTION OF EARLY STAGE PANCREATIC CANCER

This application is a national phase application under 35 U.S.C. § 371 of International Application No. PCT/US2018/019548, filed Feb. 23, 2018, which claims the benefit of U.S. Provisional Patent Application No. 62/463,348, filed Feb. 24, 2017, the entirety of each of which is incorporated herein by reference.

This invention was made with government support under grant number CA111302 awarded by the National Institutes of Health. The government has certain rights in the invention.

BACKGROUND

1. Field of the Invention

The present invention relates generally to the fields of molecular biology and medicine. More particularly, it concerns biomarkers for the early detection of pancreatic cancer.

2. Description of Related Art

Pancreatic ductal adenocarcinoma (PDAC) is the fourth leading cause of cancer deaths in the United States with most patients presenting with locally advanced disease (~30%) or distant metastasis (~50%) when surgical resection is no longer a curative option (Conlon et al., 1996; Rahib et al., 2014). The impact of diagnosis of PDAC at earlier, resectable stages is estimated to improve 5 year survival to 30% or more, suggesting that death rates for PDAC patients would be substantially reduced if the disease could be diagnosed early (Chu et al., 2010).

Unfortunately, there are no biomarkers that detect early stage PDAC. The current gold standard blood-based biomarker CA 19-9 lacks the specificity needed for early detection of the disease (Chu et al., 2010). Attempts to identify PDAC biomarkers have failed to produce a single marker or combination of markers that stand up to multiple blinded validations and improve CA19-9. Thus, there is an unmet need for a novel biomarker panel to improve the current gold standard biomarker for early detection of PDAC.

SUMMARY OF THE INVENTION

Certain embodiments of the present disclosure concern a biomarker panel for the detection of cancer, particularly early detection of pancreatic cancer. In a first embodiment, there is provided an assay for measuring the expression of the antigens TNC-FN III-C, TFPI, and CA19-9 comprising contacting a plurality of antigens with an anti-TNC-FN III-C antibody, an anti-TFPI antibody, and an anti-CA19-9 antibody to form antigen-antibody complexes; and detecting the antigen-antibody complexes using detectable moieties that distinctly bind each of the antibodies, thereby measuring the expression of the antigens TNC-FN III-C, TFPI, and CA19-9. In some aspects, the assay is an in vitro or in vivo assay.

In some aspects, the plurality of antigens are obtained from a biological sample. In certain aspects, in the biological sample is a tissue, surgical or biopsy specimen, a paraffin embedded tissue, a frozen tissue imprint, peripheral blood, urine, or a fine needle aspirate. In particular aspects, the sample is a blood sample, such as a plasma sample. In some aspects, the biological sample is obtained from a subject at risk for cancer, such as a subject who has a family history of inherited cancer. In particular aspects, the biological sample is obtained from a subject over the age of 50, such as 60, 65, 70, 75, or higher. In some aspects, the subject has not been previously diagnosed with cancer. In certain aspects, the subject has not been tested for diabetes and/or chronic pancreatitis. In other aspects, the subject has been tested and been determined to not have diabetes and/or chronic pancreatitis.

In certain aspects, detecting is further defined as performing an enzyme-linked immunosorbent assay (ELISA), western blot, or immunohistochemistry. In some aspects, one, two, or three ELISAs are performed. In particular aspects, the ELISA is a sandwich ELISA. In specific aspects, the sandwich ELISA is a multiplex ELISA, wherein two or three antigens are simultaneously detected. In some aspects, the antibodies are conjugated to a surface. In certain aspects, the method further comprises washing after forming the antigen-antibody complexes to remove antigens not in an antigen-antibody complex. In some aspects, the method further comprises adding detection antibodies specific for each of the three antigens after the washing step. In particular aspects, the detecting antibodies are biotinylated. Accordingly, in some aspects, detecting comprises adding streptavidin-conjugated fluorophores and measuring the fluorophores.

In some aspects, the sample is undiluted. In other aspects, the sample is diluted at least 50-fold, such as at least 75-fold, 100-fold, 150-fold, 200-fold, or higher.

In some aspects, the detectable moieties are bound to the antibodies prior to contacting the antibodies with the plurality of antigens. In some aspects, the detectable moieties comprise fluorescent probes, radioactive probes, or photosensitizers. In particular aspects, the fluorescent probes comprise indocyanine green (ICG), fluoresceine isothiocyanate (FITC), and/or IRDye800. In some aspects, the detectable moieties bound to the antibodies are detected by optical imaging, ultrasound, magnetic resonance imaging (MRI), positron emission tomography (PET), single-photon emission computed tomography (SPECT), or phototherapy. In some aspects, the plurality of antigens are comprised in a tissue. In certain aspects, the tissue is a tumor. In particular aspects, the tissue is human tissue.

In certain aspects, measuring comprises comparing the expression of each of the three antigens to the expression in a control sample. In some aspects, the control sample is isolated from a healthy subject. In other aspects, the control sample is isolated from a subject with benign disease. In certain aspects, an increased expression of the three antigens as compared to a control sample indicates the presence of cancer or a precursor lesion.

In some aspects, the method further comprises performing further diagnostic assays, such as imaging studies, for pancreatic cancer. In some aspects, the cancer is pancreatic cancer, such as early stage pancreatic cancer. In particular aspects, the early stage pancreatic cancer is Stage I (e.g., Stage IA or Stage IB) or Stage II (e.g., Stage IIA or Stage IIB) pancreatic cancer. In some aspects, the precursor lesion is a pancreatic cancer precursor lesion (PanIN).

In some aspects, the specificity of the assay is at least 0.8, such as 0.81, 0.82, 0.83, 0.84, 0.85, 0.86, 0.87, 0.88, 0.89, 0.90 or higher. In certain aspects, the accuracy of the assay is at least 0.7, such as 0.71, 0.72, 0.73, 0.74, 0.75, 0.76, 0.77, 0.78, 0.79, 0.80, or higher. In particular aspects, the AUC of the assay is at least 0.90, such as 0.91, 0.92, 0.93, 0.94, 0.95, 0.96, 0.97, 0.98, 0.99 or higher.

In some aspects, the method further comprises analyzing covariates of the subject in combination with the presence of the three antigens. In certain aspects, the covariates comprise age, sex, center, smoking, and/or drinking In some aspects, logistic regression models may be used to develop combinations of the biomarker panel plus age, sex, center, smoking and drinking for separating patient case and healthy or benign disease.

In another embodiment, the present disclosure further provides a method of treating pancreatic cancer in a subject comprising administering one or more anti-cancer therapies to the subject, wherein the subject is identified to have increased expression of the antigens TNC-FN III-C, TFPI, and CA19-9 as compared to expression of the antigens in a control. In some aspects, the control is a healthy subject.

In certain aspects, the increased expression of the antigens is determined by performing ELISA on a sample obtained from the subject. In particular aspects, the increased expression of the antigens is determined according to the methods of the embodiments (e.g., contacting a plurality of antigens with an anti-TNC-FN III-C antibody, an anti-TFPI antibody, and an anti-CA19-9 antibody to form antigen-antibody complexes; and detecting the antigen-antibody complexes using detectable moieties that distinctly bind each of the antibodies, thereby measuring the expression of the antigens TNC-FN III-C, TFPI, and CA19-9). In some aspects, the sample is a plasma sample. In particular aspects, the pancreatic cancer is early stage pancreatic cancer.

In some aspects, the one or more anti-cancer therapies are chemotherapy, radiotherapy, gene therapy, surgery, hormonal therapy, anti-angiogenic therapy, and/or immunotherapy.

In yet another embodiment, there is provided a kit for detecting pancreatic cancer comprising a set of antibodies specific for the antigens TNC-FN III-C, TFPI, and CA19-9. The kit may further comprise reagents, such as plates or arrays, wash solutions and detections reagents, to perform an ELISA or other antibody detection assay.

A further embodiment provides a method for detecting a cancer cell comprising obtaining a biological sample; contacting the biological sample with an anti-TNC-FN III-C antibody, an anti-TFPI antibody, and an anti-CA19-9 antibody; and detecting binding of the anti-TNC-FN III-C antibody, anti-TFPI antibody, and anti-CA19-9 antibody to the sample, wherein increased expression of the three antigens as compared to a control indicates the presence of a cancer cell. In some aspects, the method is in vitro or in vivo.

In certain aspects, in the biological sample is a surgical or biopsy specimen, a tissue, a paraffin embedded tissue, a frozen tissue imprint, peripheral blood, urine, or a fine needle aspirate. In particular aspects, the sample is a blood sample, such as a plasma sample. In some aspects, the biological sample is obtained from a subject at risk for cancer, such as a subject who has a family history of inherited cancer. In particular aspects, the biological sample is obtained from a subject over the age of 50. In some aspects, the subject has not been previously diagnosed with cancer. In certain aspects, the subject has not been tested for diabetes and/or chronic pancreatitis. In other aspects, the subject has been tested and been determined to not have diabetes and/or chronic pancreatitis.

In certain aspects, detecting is further defined as performing an ELISA. In some aspects, one, two, or three ELISAs are performed. In particular aspects, the ELISA is a sandwich ELISA. In specific aspects, the sandwich ELISA is a multiplex ELISA, wherein two or three antigens are simultaneously detected. In some aspects, the antibodies of are conjugated to a surface. In certain aspects, the method further comprises washing after forming the antibody-antigen complexes to remove antigens not in an antigen-antibody complex. In some aspects, the method further comprises adding detection antibodies specific for each of the three antigens after the washing step. In particular aspects, the detecting antibodies are biotinylated. Accordingly, in some aspects, detecting comprises adding streptavidin-conjugated fluorophores and measuring the fluorophores.

In some aspects, the sample is undiluted. In other aspects, the sample is diluted at least 50-fold, such as at least 75-fold, 100-fold, 150-fold, 200-fold, or higher.

In certain aspects, measuring comprises comparing the expression of each of the three antigens to the expression in a control sample. In some aspects, the control sample is isolated from a healthy subject. In other aspects, the control sample is isolated from a subject with benign disease. In some aspects, the cancer is pancreatic cancer, such as early stage pancreatic cancer. In particular aspects, the early stage pancreatic cancer is Stage I (e.g., Stage IA or Stage IB) or Stage II (e.g., Stage IIA or Stage IIB) pancreatic cancer. In some aspects, the precursor lesion is a PanIN lesion.

In some aspects, the specificity of the assay is at least 0.8, such as 0.81, 0.82, 0.83, 0.84, 0.85, 0.86, 0.87, 0.88, 0.89, 0.90 or higher. In certain aspects, the accuracy of the assay is at least 0.7, such as 0.71, 0.72, 0.73, 0.74, 0.75, 0.76, 0.77, 0.78, 0.79, 0.80, or higher. In particular aspects, the AUC of the assay is at least 0.90, such as 0.91, 0.92, 0.93, 0.94, 0.95, 0.96, 0.97, 0.98, 0.99 or higher.

In another embodiment, there is provided a method of measuring the expression of the antigen TFPI comprising contacting a plurality of antigens with an anti-TFPI antibody to form antigen-antibody complexes; and detecting the antigen-antibody complexes using detectable moieties that distinctly bind the anti-TFPI antibody, thereby measuring the expression of the antigen TFPI, wherein an increased expression of TFPI compared to a control indicated the presence of a precancerous lesion. In some aspects, the precancerous lesion is a PanIN lesion. In certain aspects, the detecting is further defined as performing an ELISA. In certain aspects, the detecting is further defined as performing immunohistochemistry or western blot, or any method known in the art for the detection of antibody-antigen complexes.

In certain aspects, the plurality of antigens are obtained from a biological sample. In some aspects, the biological sample is a surgical or biopsy specimen, tissue, a paraffin embedded tissue, a frozen tissue imprint, peripheral blood, urine, or a fine needle aspirate. In some aspects, the blood sample is a plasma sample. In certain aspects, the biological sample is obtained from a subject at risk for cancer or who has a family history of inherited cancer.

In certain aspects, the detectable moieties are conjugated to the antibodies prior to contacting the antibodies to the plurality of antigens. In some aspects, the detectable moieties comprise fluorescent probes, radioactive probes, or photosensitizers. In certain aspects, the detectable moieties conjugated to the antibodies are detected by optical imaging, ultrasound, magnetic resonance imaging (MRI), positron emission tomography (PET), single-photon emission computed tomography (SPECT), or phototherapy.

In some aspects, the method further comprises analyzing covariates of the subject in combination with the presence of the three antigens. In certain aspects, the covariates comprise age, sex, center, smoking, and/or drinking.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2D: Biomarker panel performance in the EDRN reference set cohort 3. [2A] ROC curves of the biomarker panel in differentiating Stage IA/IB/IIA from healthy controls. [2B] ROC curves of the biomarker panel in differentiating Stage IA/IB/IIA from healthy controls in cohort without history of diabetes and pancreatitis. [2C] ROC curves of the biomarker panel in differentiating Stage IIB from healthy controls. [2D] ROC curves of the biomarker panel in differentiating Stage IIB from healthy controls in samples without history of diabetes and chronic pancreatitis. AUC were calculated, and its 95% CI was estimated using bootstrapping method. P-values are two sided and based on Z-test using bootstrap standard error estimate. Abbreviations: AUC, area under the curve.

DESCRIPTION OF ILLUSTRATIVE EMBODIMENTS

Figure 1A:
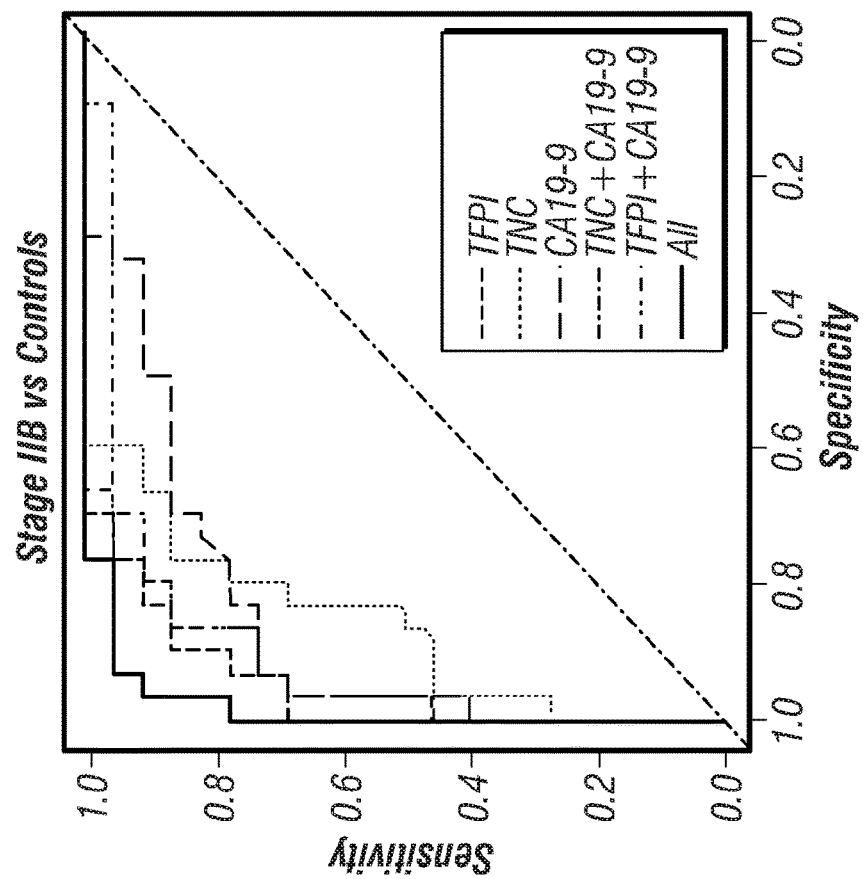
FIGS. 1A-1D: Biomarker panel performance in the TexGen cohort 1. Receiver operating characteristics (ROC) curves of the biomarker panel in differentiating Stage I/IIA [1A], Stage IIB [1B], all Stage II [1C] and all early stage cancer [1D] from healthy controls in the TexGen cohort. AUC were calculated, and its 95% confidence interval (CI) was estimated using bootstrapping method. The P values were two-sided and are based on bootstrapping.

Greater than 90% of pancreatic adenocarcinoma (PDAC) patients die from their disease, making detection of early stage disease critically important. Detected at a resectable stage, PDAC 5-year survival is estimated as high as 30% at major centers, 30-60% for node-negative tumors <2 cm and 60% for extremely small tumors of approximately <10 mm (Ryan et al., 2014; Mayo et al., 2012; Ishikawa et al., 1999; Tsuchiyya et al., 1986). The current gold standard blood-based biomarker CA19-9 lacks the predictive value necessary for early detection. While some studies have identified markers that may improve CA19-9 performance, these studies are limited to late stage pancreatic cancer or biomarkers have not been tested using multiple blinded validation studies in early stage pancreatic cancer. Furthermore, current biomarkers have not been shown to have high enough sensitivity and specificity for general population screening. In general, assays use DNA, microRNA, or multiplex proteomic approaches with large numbers of markers that are difficult, time consuming, and expensive to translate to the clinic.

Certain embodiments of the present disclosure provide a biomarker panel for the detection of pancreatic cancer, particularly early stage pancreatic cancer as well as precancerous lesions, such as PanIN lesions. The biomarker panel provided was tested in multiple blinded validations and significantly improved the performance and accuracy of CA19-9, especially in the large and well annotated cohort of early stage samples used in the present studies. In addition, the biomarker panel of the present disclosure may be used in the clinic, such as one or more sandwich ELISA assays (e.g., a multiplex ELISA for screening all three biomarkers) that are easy to use, provide quick results, and require a single blood sample. Interestingly, the present biomarker panel may be used for screening of the general population as it was shown to be independent of diabetes and chronic pancreatitis status.

Specifically, the present studies have identified the optimized isoform TNC-FN III-C as a novel biomarker for pancreatic cancer. It was found that TNC-FN III-C and TFPI improve the performance of CA19-9. The panel of the three biomarkers was validated in two blinded validations using large sample cohorts of early stage pancreatic cancer and was shown to consistently increase the performance of CA19-9. Thus, the panel adds statistical significance to CA 19-9's predictive power to detect early stage PDAC, and thus has clinical utility as an assay for early detection of surgically resectable PDAC.

Accordingly, one method provided herein comprises determining the presence of pancreatic cancer, including early stage pancreatic cancer, by detecting altered levels of the biomarker panel TNC-FN III-C, TFPI, and CA19-9 as compared to healthy or benign disease controls. The biomarkers may be measured by ELISA, western blot, immunohistochemistry, or other antibody-based detection methods. The method may comprise antibodies bound to imaging agents, such as fluorophores or radioisotopes, which may be detected by optical imaging or ultrasound. Subjects identified to have altered levels of expression of the biomarker panel may be treated for pancreatic cancer or may be referred for imaging studies and further clinical tests for early detection of pancreatic cancer.

In addition, the present studies found that TFPI may be used as a biomarker of precancerous lesions, such as PanIN lesions. Accordingly, further embodiments provide methods of measuring TFPI in a sample or tissue, such as for the detection of PanIN lesions.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein, the term "subject" refers to a human or non-human mammal or animal. Non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments, a subject is a patient. As used herein, a "patient" refers to a subject who is under the care of a physician or other health care worker, including someone who has consulted with, received advice from or received a prescription or other recommendation from a physician or other health care worker.

The term "treatment" or "treating" is intended to include prophylaxis, amelioration, prevention or cure of a condition (e.g., pancreatic cancer). Treatment after a condition (e.g., pancreatic cancer) that has started aims to reduce, ameliorate or altogether eliminate the condition, and/or its associated symptoms, or prevent it from becoming worse. Treatment of subjects before a condition has started aims to reduce the risk of developing the condition and/or lessen its severity if the condition does develop. As used herein, the term "prevent" refers to the prophylactic treatment of a subject who is at risk of developing a condition resulting in a decrease in the probability that the subject will develop the disorder, and to the inhibition of further development of an already established disorder.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "antibody" herein is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

The term "determining an expression level" as used herein means the application of a gene specific reagent such as a probe, primer or antibody and/or a method to a sample, for example a sample of the subject and/or a control sample, for ascertaining or measuring quantitatively, semi-quantitatively or qualitatively the amount of a gene or genes, for example the amount of mRNA. For example, a level of a gene can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR, serial analysis of gene expression (SAGE), Northern Blot, digital molecular barcoding technology, for example Nanostring: nCounter™ Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene® ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and for example for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by fine needle aspiration that is directed to a target, such as a tumor, or is random sampling of normal cells, such as periareolar), any other bodily fluid, a tissue (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet.

The terms "increased", "elevated", "overexpress", "overexpression", "overexpressed", "up-regulate", or "up-regulated" interchangeably refer to a biomarker that is present at a detectably greater level in a biological sample, e.g. plasma, from a patient with cancer, in comparison to a biological sample from a patient without cancer. The term includes overexpression in a sample from a patient with cancer due to transcription, post-transcriptional processing, translation, post-translational processing, cellular localization (e.g., organelle, cytoplasm, nucleus, cell surface), and RNA and protein stability, as compared to a sample from a patient without cancer. Overexpression can be detected using conventional techniques for detecting mRNA (i.e., RT-PCR, PCR, hybridization) or proteins (i.e., ELISA, immunohistochemical techniques, mass spectroscopy, Luminex® xMAP technology). Overexpression can be 10%, 20%, 30%, 40%, 50%, 60%, 70%, 80%, 90% or more in comparison to a sample from a patient without cancer. In certain instances, overexpression is 1-fold, 2-fold, 3-fold, 4-fold 5, 6, 7, 8, 9, 10, or 15-fold or more higher levels of transcription or translation in comparison to a sample from a patient without cancer.

A "label," "imaging agent"" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

As used herein, the term "biomarker" refers to any biological feature from tissue sample or a cell to be identified or quantitated. A biomarker can be useful or potentially useful for measuring the initiation, progression, severity, pathology, aggressiveness, grade, activity, disability, mortality, morbidity, disease sub-classification or other underlying feature of one or more biological processes, pathogenic processes, diseases, or responses to a therapeutic intervention. A biomarker is virtually any biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the sample to be analyzed and that can be isolated from, or measured in, the sample.

As used herein, the term "detecting" refers to observing a signal from a label moiety to indicate the presence of a biomarker in the sample. Any method known in the art for detecting a particular detectable moiety can be used for detection. Exemplary detection methods include, but are not limited to, spectroscopic, photochemical, biochemical, immunochemical, electrical, optical or chemical methods.

II. PANCREATIC CANCER DETECTION

A. Biological Sample

Certain embodiments of the present disclosure concern the detection and quantification of the expression of certain antigens or biomarkers (e.g., TNC-FN IIIC, TFPI, and/or CA19-9) in a sample. As used herein, the term "biological sample" may refer to a whole organism or a subset of its tissues, cells or component parts. A "biological sample" may also refer to a homogenate, lysate, or extract prepared from a whole organism or a subset of its tissues, cells or component parts, or a fraction or portion thereof. Typically, the biological sample is diluted prior to performing an assay. Non-limiting examples of biological samples include urine, blood, cerebrospinal fluid (CSF), pleural fluid, sputum, and peritoneal fluid, bladder washings, secretions, oral washings, tissue samples, touch preps, or fine-needle aspirates.

The sample may comprise body fluids and tissue samples that include but are not limited to blood, tissue biopsies, spinal fluid, meningeal fluid, urine, alveolar fluid. In some embodiments, a biological sample may be a cell line, cell culture or cell suspension. Preferably, a biological sample corresponds to the amount and type of DNA and/or expression products present in a parent cell from which the sample was derived. A biological sample can be from a human or non-human subject. In particular embodiments, the sample is a plasma sample. The assay may also be applied to in vivo tissue, such as during a surgery.

B. Biomarkers

The present disclosure provides a biomarker panel for the detection of pancreatic cancer. The panel include the biomarkers TNC-FN III-C, TFPI, and CA19-9. Both TNC-FN III-C and TFPI increase the performance of CA19-9 in the detection of pancreatic cancer as a two-marker panel (e.g., TNC-FN III-C/CA19-9 or TFPI/CA19-9) and as a three-marker panel (e.g., TNC-FN III-C/TFPI/CA19-9). The present biomarker panel improves upon the AUC, specificity, and sensitivity and accuracy of the CA19-9 gold standard assay to detect pancreatic cancer. By increasing the specificity of the assay by the addition of TNC-FN III-C the panel cuts the number of false positive cases to such a degree that patients could be sent for further imaging tests such as CT scans, MRI or ultrasound.

1. CA19-9

CA19-9 is a tumor-associated mucin glycoprotein antigen that is related to the Lewis blood group protein. While a high CA 19-9 is most commonly associated with pancreatic cancer, other cancers, such as colorectal, lung, and gallbladder cancers, can also cause elevated levels. High CA 19-9 levels can also be caused by non-cancerous conditions such as gallstones, a blockage of the bile duct (jaundice), pancreatitis, cystic fibrosis, and liver disease.

An ideal tumor marker should be specific to a given tumor type and highly sensitive in order to refrain from a false positive diagnosis. However, CA 19-9 does not appear to fit these criteria due to its inadequate sensitivity, false negative results in the Lewis blood type negative (Lea-b-) population, and high false-positive results induced by obstructive jaundice (10-60%) (Wu et al., 2013).

2. TNC-FN III-C

Tenascin-C is an extracellular matrix glycoprotein that is composed of four domains. One subunit has a TA domain at the N-terminal end, then an epidermal growth factor-like sequence domain (EGF-like domain), a fibronectin type III (FN III) repeat domain, and a fibrinogen-like domain at the C-terminal end. There is an alternatively spliced domain in the FN III domain, and it generates some types of variants of Tenascin-C. The subunits form a trimer by twisting at the N-terminal coiled domain and form a hexamer by a disulfide bond, in tissue. While low molecular weight variants of Tenascin-C are present in normal tissue, the present disclosure identified a high molecular variant of Tenascin-C, TNC-FN III-C expressed in pancreatic cancer. Thus, the present studies are the first to identity this isoform as a biomarker for pancreatic cancer.

3. TFPI

Tissue factor pathway inhibitor (TFPI) is an anti-coagulation protein that acts as a Kunitz-type serine protease inhibitor. TFPI is a single-chain polypeptide which can reversibly inhibit Factor Xa. While Xa is inhibited, the Xa-TFPI complex can subsequently also inhibit the FVIIa-tissue factor complex. FPI is thought to be important in modulating TF-induced thrombogenesis, since inappropriate thrombus formation in blood vessels can cause cardiovascular diseases such as myocardial infarction, stroke, and pulmonary embolism, amongst others. TFPI may be used as a biomarker, alone or combination, for the detection of precancerous lesions, such as PanINs.

C. Detection Methods

The level of expression of the biomarker panel may be measured by ELISA, western blotting, mass spectrometry, a capillary immune-detection method, isoelectric focusing, an immune precipitation method or immunohistochemistry. Other methods include of detection include antibody-based optical imaging, ultrasound imaging, MRI imaging, PET imaging, and phototherapy. In particular embodiments, the present methods concern performing one or more ELISA assays for detecting the expression of one or more biomarkers, such as TNC-FN IIIC, TFPI, and CA19-9.

An enzyme-linked immunosorbent assay, or ELISA, may be used to measure the differential expression of a plurality of biomarkers. There are many variations of an ELISA assay. ELISA tests may be formatted for direct, indirect, competitive, or sandwich detection of the analyte. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. The primary antibodies are conjugated to a detection system, such as an enzyme that produces a detectable product. The antibody-antibody complexes may be detected indirectly. For example, the primary antibody is detected by a secondary antibody that is conjugated to a detection system, as described above. The microtiter plate is then scanned and the raw intensity data may be converted into expression values using means known in the art. Single- and Multi-probe kits are available from commercial suppliers, e.g., Meso Scale Discovery (MSD).

In one ELISA method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the ELISA is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

In certain embodiments, the biomarker or antibody bound to the biomarker is directly or indirectly labeled with a detectable moiety. The role of a detectable agent is to facilitate the detection step of the diagnostic method by allowing visualization of the complex formed by binding of the binding agent to the protein marker (or fragment thereof). The detectable agent can be selected such that it generates a signal that can be measured and whose intensity is related (preferably proportional) to the amount of protein marker present in the sample being analyzed. Methods for labeling biological molecules such as polypeptides and antibodies are well-known in the art. Any of a wide variety of detectable agents can be used in the practice of the present disclosure. Suitable detectable agents include, but are not limited to: various ligands, radionuclides, fluorescent dyes, chemiluminescent agents, microparticles (such as, for example, quantum dots, nanocrystals, phosphors and the like), photosensitizers, enzymes (such as, those used in an ELISA, i.e., horseradish peroxidase, beta-galactosidase, luciferase, alkaline phosphatase), colorimetric labels, magnetic labels, and biotin, digoxigenin or other haptens and proteins for which antisera or monoclonal antibodies are available.

The antibodies may be attached to imaging agents of use for imaging and diagnosis of various diseased organs, tissues or cell types. The antibody may be labeled or conjugated with a fluorophore or radiotracer for use as an imaging agent. Many appropriate imaging agents are known in the art, as are methods for their attachment to proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase). In some embodiments, the imaging conjugate will also be dual labeled with a radio-isotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), or intrathecal injection, or as described in greater detail below.

In some aspects, the imaging agent is a chromophore, such as a fluorophore. Exemplary fluorophores suitable for use with the present disclosure includes rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine; cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, pro flavin, acridine orange, acridine yellow, arylmethine derivatives, auramine, crystal violet, malachite green, tetrapyrrole derivatives, porphin, phtalocyanine and bilirubin; 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), Fluorescein dT, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ RholO1, ATTO™ 590, ATTO™ 633, ATTO™ 647N, TYE™ 563, TYE™ 665, and TYE™ 705. In particular aspects, the chromophore is TAMRA.

The detectable moiety may include, but is not limited to fluorodeoxyglucose (FDG); 2'-fluoro-2'deoxy-1beta-D-arabionofuranosyl-5-ethyl-uracil (FEAU); 5-[$^{123}$I]-2'-fluoro-5-iodo-1β-D-arabinofuranosyl-uracil; 5-[$^{124}$I]-2'-fluoro-5-iodo-1β-D-arabinofuranosyl-uracil; 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil; 2-[$^{11}$I]- and 5-([$^{11}$C]methyl)-2'-fluoro-5-methyl-1-β-D-arabinofuranosyl-uracil; 2-[$^{11}$C]-2'-fluoro-5-ethyl-1-β-D-arabinofuranosyl-uracil; 5-([$^{11}$C]-ethyl)-2'-fluoro-5-ethyl-1-β-D-arabinofuranosyl-uracil; 5(2-[$^{18}$F]-ethyl)-2'-fluoro-5-(2-fluoro-ethyl)-1-β-D-arabinofuranosyl-uracil, 5-[$^{123}$I]-2'-fluoro-5-iodovinyl-1-β-D-arabinofuranosyl-uracil; 5-[$^{124}$I]-2'-fluoro-5-iodovinyl-1-β-D-arabinofuranosyl-uracil; 5-[$^{131}$I]-2'-fluoro-5-iodovinyl-1-β-D-arabinofuranosyl-uracil; 5-[$^{123}$I]-2'-fluoro-5-iodo-1-β-D-ribofuranosyl-uracil; 5-[$^{124}$I]-2'-fluoro-5-iodo-1-β-D-ribofuranosyl-uracil; 5-[$^{131}$I]-2'-fluoro-5-iodo-1-β-D-ribofuranosyl-uracil; 5-[$^{123}$I]-2'-fluoro-5-iodovinyl-1-β-D-ribofuranosyl-uracil; 5-[$^{124}$I]-2'-fluoro-5-iodovinyl-1-β-D-ribofuranosyl-uracil; 5-[$^{131}$I]-2'-fluoro-5-iodovinyl-1-β-D-ribofuranosyl-uracil; or 9-4-[$^{18}$F]fluoro-3-(hydroxymethyl)butyl]guanine.

In some aspects, the imaging agent is a radionuclide. Suitable radionuclide labels are Tc, In, Ga, Cu, F, Lu, Y, Bi, Ac, and other radionuclide isotopes. Particularly, the radionuclide is selected from the group comprising $^{111}$In, $^{99m}$Tc, $^{94m}$Tc, $^{67}$Ga, $^{66}$Ga, $^{68}$Ga, $^{52}$Fe, $^{69}$Er, $^{72}$As, $^{97}$Ru, $^{203}$Pb, $^{62}$Cu, $^{64}$Cu, $^{67}$Cu, $^{186}$Re, $^{188}$Re, $^{86}$Y, $^{90}$Y, $^{51}$Cr, $^{52m}$Mn, $^{157}$Gd, $^{177}$Lu, $^{161}$Tb, $^{169}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Su, $^{177m}$Sn, $^{213}$Bi, $^{142}$Pr, $^{143}$Pr, $^{198}$Au, $^{199}$Au, $^{18}$F, $^{123}$I, $^{124}$I, $^{131}$I, $^{75}$Br, $^{76}$Br, $^{77}$Br, and $^{82}$Br, amongst others. These radionuclides are cationic and can be complexed with the chelator through the chelating group of the conjugate to form labeled compositions.

Methods of detecting and/or for quantifying a detectable label or signal generating material depend on the nature of the label. The products of reactions catalyzed by appropriate enzymes can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers. Any of the methods for detection can be performed in any format that allows for any suitable preparation, processing, and analysis of the reactions. This can be, for example, in multi-well assay plates (e.g., 96 wells or 386 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label. Imaging may be by optical imaging, ultrasound, PET, SPECT, MRI, or phototherapy.

In some aspects, the one or more assays may be sandwich ELISA assays. The three biomarkers may be detected by three separate ELISA assays, such as on three separate plates or slide for each biomarker or one plate or slide with separate wells for each biomarker.

In certain embodiments, the antigen-specific antibodies may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex®, Sepharose®, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

In other aspects, the three biomarkers may be detected by a multiplex ELISA to detect two or three of the biomarkers simultaneously. For example, the multiplex ELISA may comprise an antibody array with capture antibodies spotted in subarrays on which the sample is incubated, non-specific proteins are washed off, and the array is incubated with a cocktail of biotinylated detection antibodies followed by a streptavidin-conjugated fluorophore which is visualized by a fluorescence laser scanner (e.g., Quantibody Multiplex ELISA Array, RayBiotech).

The presence of several different biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations. In certain embodiments, such methods employ an array, wherein multiple binding agents (for example, capture antibodies) specific for multiple biomarkers are immobilized on a substrate, such as a membrane, with each capture antibody being positioned at a specific, pre-determined, location on the substrate. Methods for performing assays employing such arrays include those described, for example, in US Patent Publication Nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

An antibody microarray may also be used to measure the differential expression of a plurality of biomarkers. For this, a plurality of antibodies is arrayed and covalently attached to the surface of the microarray or biochip. A protein extract containing the biomarker proteins of interest is generally labeled with a fluorescent dye or biotin. The labeled biomarker proteins are incubated with the antibody microarray. After washes to remove the unbound proteins, the microarray is scanned. The raw fluorescent intensity data may be converted into expression values using means known in the art.

D. Imaging

In certain embodiments, this disclosure contemplates methods of imaging of target antigens using antibodies with detectable moieties. The antibody can be labeled with fluorescence and/or radioactivity which can be detected by various methods known in the art.

Nuclear Magnetic Resonance (NMR) and Magnetic Resonance Imaging (MRI) are techniques for identifying isotopes in a sample (area) by subjecting the sample to an external magnetic fields and detecting the resonance frequencies of the nuclei. An MRI scanner typically consists of magnet of 1.5 to 7, or more Tesla strength. A magnetic field and radio waves are used to excite protons in the body. These protons relax after excitation, and a computer program translates this data into pictures of human tissue. In certain embodiments, this disclosure contemplates that a pre-contrast image is taken. Once the composition is injected, a post-contrast image is taken.

NMR typically involves the steps of alignment (polarization) of the magnetic nuclear spins in an applied, constant magnetic field and perturbation of this alignment of the nuclear spins by employing an electro-magnetic radiation, usually radio frequency (RF) pulse. A pulse of a given carrier frequency contains a range of frequencies centered about the carrier frequency. The Fourier transform of an approximately square wave contains contributions from the frequencies in the neighborhood of the principal frequency. The range of the NMR frequencies allows one to use millisecond to microsecond radio frequency pulses.

Single-photon emission computed tomography (SPECT) is an imaging technique using gamma rays. Using a gamma camera, detection information is typically presented as cross-sectional slices and can be reformatted or manipulated as required. One injects a gamma-emitting radioisotope (radionuclide) into a subject. The radioisotope contains or is conjugated to a molecule that has desirable properties, e.g., a marker radioisotope has been attached to a ligand, folate. This allows the combination of ligand, e.g., folate, and radioisotope (the radiopharmaceutical) to be carried and bound to a place of interest in the body, which then (due to the gamma-emission of the isotope) allows the ligand concentration to be seen by a gamma-camera.

Positron emission tomography (PET) is an imaging technique that produces a three-dimensional image. The system detects pairs of gamma rays emitted indirectly by a positron-emitting radionuclide (tracer). Three-dimensional images of tracer concentration within the area are then constructed by computer analysis. A radioactive tracer isotope is injected into subject, e.g., into blood circulation. Typically there is a waiting period while tracer becomes concentrated in tissues of interest; then the subject is placed in the imaging scanner. As the radioisotope undergoes positron emission decay, it emits a positron, an antiparticle of the electron with opposite charge, until it decelerates to a point where it can interact with an electron, producing a pair of (gamma) photons moving in approximately opposite directions. These are detected in the scanning device. The technique depends on simultaneous or coincident detection of the pair of photons moving in approximately opposite direction (the scanner has a built-in slight direction-error tolerance). Photons that do not arrive in pairs (i.e. within a timing-window) are ignored. One localizes the source of the photons along a straight line of coincidence (also called the line of response, or LOR). This data is used to generate an image.

Light having a wavelength range from 600 nm and 850 nm lies within the near infrared range of the spectrum, in contrast to visible light, which lies within the range from about 400 nm to about 500 nm. Therefore, the excitation light used in practice of the disclosure diagnostic methods will contain at least one wavelength of light to illuminates the tissue at the infrared wavelength to excite the compounds in order that the fluorescence obtained from the area having uptake of the compounds of the present disclosure is clearly visible and distinct from the auto-fluorescence of the surrounding tissue. The excitation light may be monochromatic or polychromatic. In this manner, the compounds of the present disclosure are advantageous as they eliminate the need for use of filtering mechanisms that would be used to obtain a desired diagnostic image if the fluorescent probe is one that fluoresces at wavelengths below about 600 nm. In this manner, the compounds of the present disclosure avoid obscured diagnostic images that are produced as a result of excitation light of wavelengths that would be reflected from healthy tissue and cause loss of resolution of the fluorescent image.

Diagnostic labs, physicians' offices and operating rooms for surgical procedures can be equipped with an overhead light that produces wavelengths of light in the optical emitting spectrum useful in practice of disclosure diagnostic methods, such as lamps that produce light in the appropriate wavelength. Such a light can be utilized in the practice of the disclosure diagnostic methods merely by turning out the other lights in the operating room (to eliminate extraneous light that would be visibly reflected from tissue in the body part under investigation) and shining the excitation light of near infrared wavelength into the body cavity or surgically created opening so that the fluorescent image received directly by the eye of the observer (e.g., the surgeon) is predominantly the fluorescent image emanating from the fluorophore(s) in the field of vision.

Within any of the imaging embodiments, methods disclosed herein may further comprise the steps of recording the images from an area of the subject on a computer or computer readable medium. In certain embodiments, the methods may further comprise transferring the recorded images to a medical professional representing the subject under evaluation.

In some aspects, the compounds of the present disclosure are used to identify a tumor by administering such compounds for a time and under conditions that allow for binding of the compound to at least one cell of the target cell type (e.g., recently recruited and differentiated macrophages). The bound compound is then optically detected such that presence of fluorescence of the near infrared wavelength emanating from the bound, targeted compound of the present disclosure indicated that the target cell type is present in the biological sample.

The amount of the conjugate compound effective for use in accordance with the method of the disclosure depends on many parameters, including the molecular weight of the conjugate, its route of administration, and its tissue distribution. The antigen-specific antibodies can be administered in one or more doses (e.g., about 1 to about 3 doses) prior to the catheterization or external imaging procedure. The number of doses depends on the molecular weight of the compound, its route of administration, and its tissue distribution, among other factors.

The antibodies may be administered parenterally to the patient being evaluated for a tumor, for example, intravenously, intradermally, subcutaneously, intramuscularly, or intraperitoneally, in combination with a pharmaceutically acceptable carrier. Suitable means for parenteral administration include needle (including microneedle) injectors, needle-free injectors and infusion techniques.

E. Methods of Use

Aspects of the present disclosure include methods for diagnosing or monitoring the onset, progression, or regression of cancer in a subject by, for example, obtaining cell or tissue samples from a subject and assaying such samples for the presence of altered expression of the three biomarkers TNF-FN III-C, TFPI, and CA19-9. As used herein, the term "cancer" refers to an uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject.

Cancers include, but are not limited to, basal cell carcinoma; biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. In particular embodiments, a subject who is diagnosed or treated by the present methods, is a subject with pancreatic cancer, such as early stage pancreatic cancer.

The methods described herein can be used to screen patients for cancer, or can be used to monitor patients diagnosed with cancer. For example, in a screening mode, patients at risk for pancreatic cancer are screened with the goal of earlier detection of bladder cancer. The methods described herein can be used alone, or in conjunction with other tests. In general, ELISA is performed on a plasma sample, and the altered expression of the biomarker panel is determined. Patients that have altered expression of the three biomarkers are further examined, and can receive appropriate treatment, if necessary. After treatment, patients are monitored for cancer recurrence using the methods described herein.

In some embodiments, a test sample may be a sample from a subject who has pancreatic cancer or a precancerous condition, while a control sample may be a sample from a subject that is free of cancer and/or free of a precancerous condition.

F. Anti-Cancer Agents

In some embodiments, the present methods identify a subject to have a cancer, such as pancreatic cancer, by detecting altered expression of the three biomarkers TNC-FN III-C, TFPI, and CA19-9. In further embodiments, the present disclosure provides methods of treating a subject identified to have a cancer by administering one or more anti-cancer therapies.

The one or more anti-cancer therapies may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The anti-cancer therapy may be in the form of adjuvant or neoadjuvant therapy.

In some embodiments, the anti-cancer therapy is the administration of small molecule enzymatic inhibitor or anti-metastatic agent. In some embodiments, the anti-cancer therapy is the administration of side-effect limiting agents (e.g., agents intended to lessen the occurrence and/or severity of side effects of treatment, such as anti-nausea agents, etc.). In some embodiments, the anti-cancer therapy is radiation therapy. In some embodiments, the anti-cancer therapy is surgery. In some embodiments, the anti-cancer therapy is a combination of radiation therapy and surgery. In some embodiments, the anti-cancer therapy is gamma irradiation. In some embodiments, the anti-cancer therapy is therapy targeting PB K/AKT/mTOR pathway, HSP90 inhibitor, tubulin inhibitor, apoptosis inhibitor, and/or chemopreventative agent. The anti-cancer therapy may be one or more of the chemotherapeutic agents known in the art.

A first anti-cancer may be administered before, during, after, or in various combinations relative to an additional cancer therapy, such as immune checkpoint therapy. The administrations may be in intervals ranging from concurrently to minutes to days to weeks. In embodiments where the first anti-cancer therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the first anti-cancer therapy and the second anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129; International Patent Publication Nos. WO 01/14424, WO 98/42752, and WO 00/37504 (CP675,206, also known as tremelimumab; formerly ticilimumab); U.S. Pat. No. 6,207,156; Hurwitz et al., 1998; Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application Nos. WO2001014424, and WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used alone or in combination with other anti-cancer therapies to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. KIT

Also within the scope of the invention are kits for performing ELISA assays on plasma samples to detect a cancer, such as pancreatic cancer. An example of such a kit may include a set of antibodies specific for the three biomarkers. The kit may further comprise instructions for use of the antibodies for performing an ELISA assay to identify altered expression of the biomarkers in the plasma samples. The kit may further comprise instructions for diagnostic purposes, indicating that elevated expression of the biomarker panel from a cancer patient indicates an increased risk for pancreatic cancer. The kit may further comprise instructions that indicate that altered expression of the biomarkers panel in a plasma indicates that a patient should be sent for further diagnostic testing and/or treated with anti-cancer agents for pancreatic cancer.

In some embodiments, a kit may further comprise detection reagents, such as streptavidin-conjugated antibodies. In some embodiments, a kit may further comprise reagents and buffers including but not limited to wash buffers. In some embodiments, a kit may further comprise mounting media and/or one or more control ELISA plates.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Analysis and Validation of Migration Signature for Pancreatic Cancer

Migration Signature Panel Validation in a Blinded CLIA-certified Clinical Laboratory Study: Clinical laboratory reproducibility of the migration signature was tested using a sandwich ELISA for TFPI (Balasenthil et al., 2011) and an optimized sandwich ELISA for TNC, using a splice-form of TNC, TNC-FN III-C, which the current studies have identified as a novel pancreatic cancer biomarker. Migration signature assays previously performed were repeated with identical samples in a blinded CLIA laboratory. Twenty PDAC stage IV plasma samples and 20 healthy controls were screened for CA 19-9, TNC-FN III-C and TFPI. Patient characteristics are presented in Table 5. Results indicated marker assays were robust and reproducible in the CLIA laboratory reaching AUCs for the combined panel of TFPI, TNC-FN III-C and CA19-9 of 0.92 (95% CI=0.82 to 1.00) in both laboratories versus an inferior performance based on CA19-9 alone (AUC 0.71, 95% CI=0.52 to 0.90 MDACC) and AUC-0.72 (95% CI=0.54 to 0.90 CLIA lab). Values of AUC and sensitivity/specificity at optimal cutoffs are presented in Table 6. These CA 19-9 assays have also previously been compared with FDA approved kits and found to have virtually identical results (Haab et al., 2015).

Figure 1B:
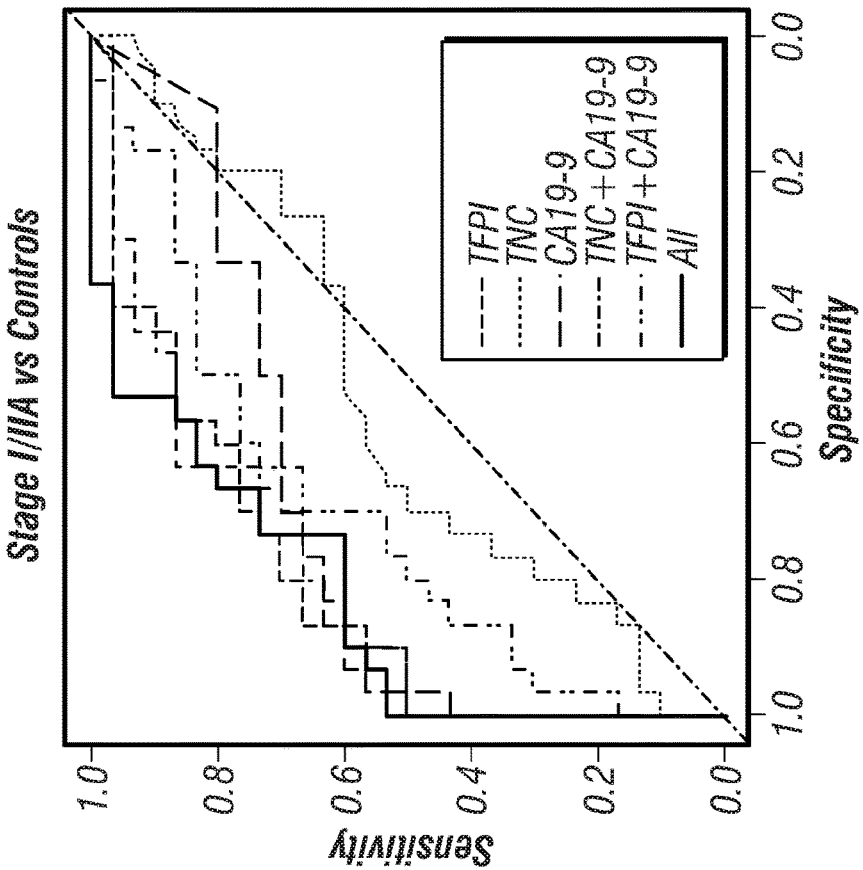
Figure 1C:
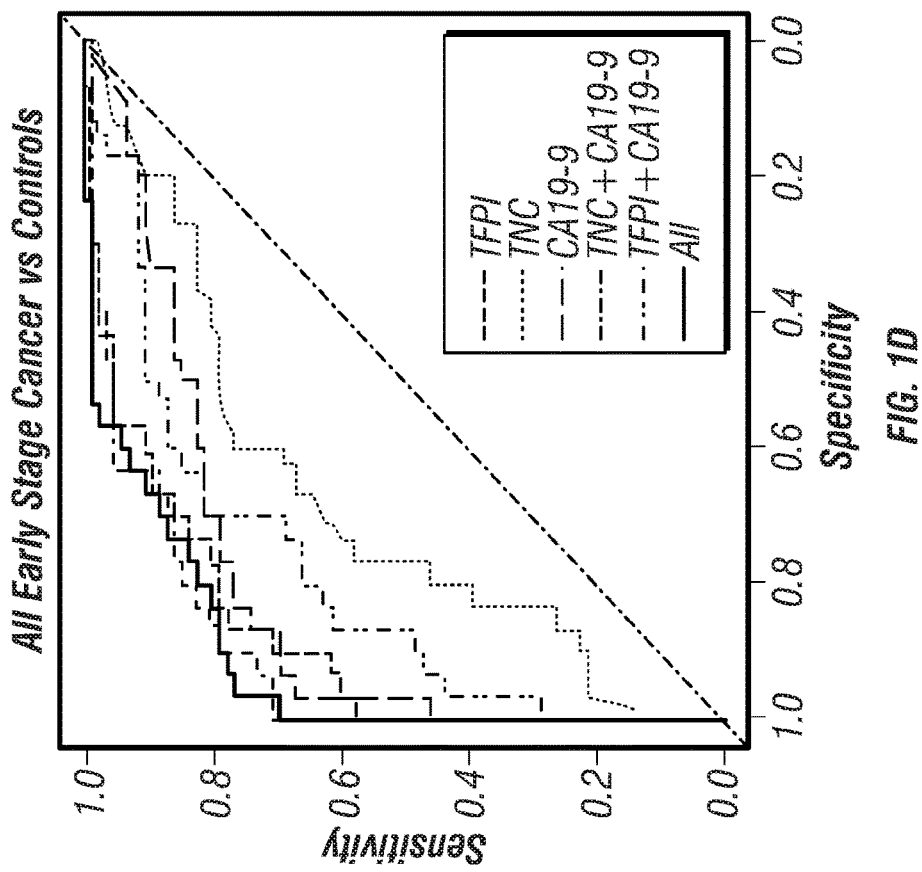
Figure 1D:
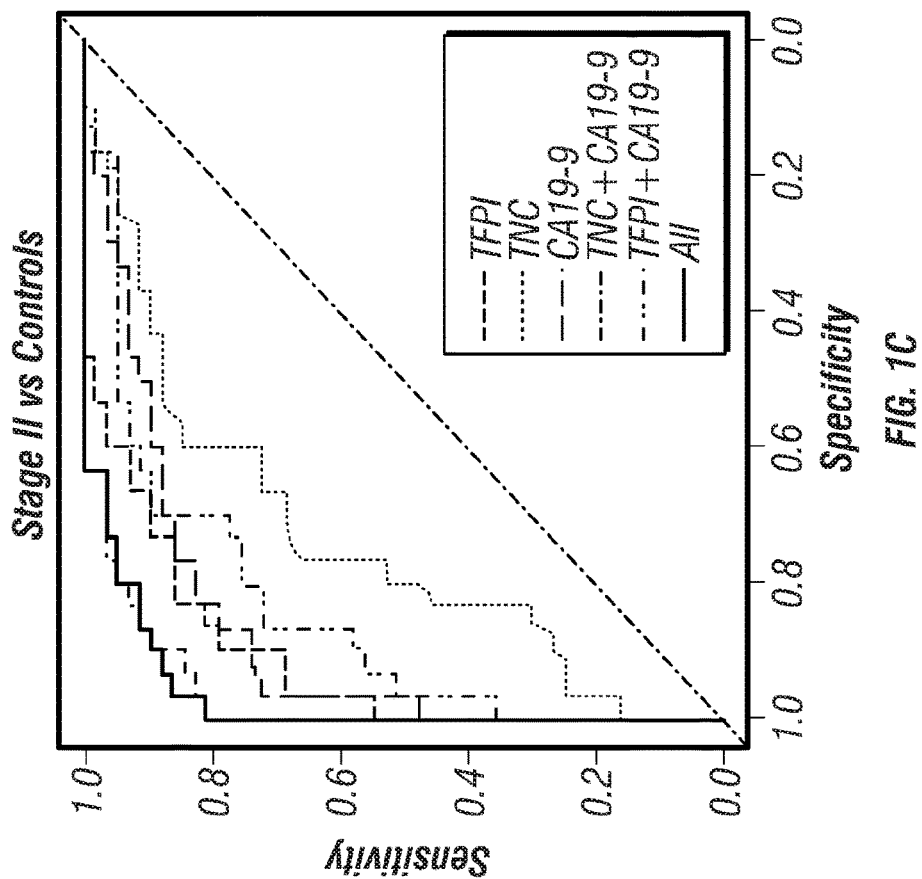

Prevalidation Studies in Early Stage PDAC: ELISA assays were next performed using an early stage plasma cohort 1 (Table 1). In the Stage IIIA PDAC cohort (n=30) versus healthy controls (n=30), migration signature markers improved the performance of CA 19-9 from an AUC of 0.72 to 0.84 (FIG. 1A and Table 2). However, in Stage IIB (n=22) compared with healthy controls, the combination of TFPI and TNC-FN III-C with the gold standard resulted in a very high AUC value of 0.98 (95% CI=0.95 to 1.00), which is statistically significantly better than that based on CA19-9 alone (FIG. 1B and Table 2). In grouping all stage II cancers together (Stage IIA/IIB) (n=57), adding TNC-FN III-C and TFPI individually improved CA 19-9 performance with AUCs of 0.92 (95% CI=0.86 to 0.97) and 0.97 (95% CI=0.94 to 0.99) respectively for TNC-FN III-C+CA 19-9 and TFPI+CA 19-9 with an overall AUC of 0.97 (95% CI=0.93 to 0.99) for the combined panel, statistically significantly improving CA19-9 (P=0.03) (FIG. 1C and Table 2). In a final analysis, the combined panel of three biomarkers was examined. Results were statistically significant for all early stage cancer (Stage I and II) (n=85) vs healthy controls (n=30) in that the migration signature panel improved the performance of CA 19-9 from an AUC of 0.83 to 0.92 (P=0.04) (FIG. 1D and Table 2).

In order to set optimal cutoffs for validation studies and for the further refinement of a diagnostic marker panel for early PDAC detection, cohort 1 was used as the training cohort to build a statistical model and risk score. Using forward selection in the comparison between all cancer and controls, the combined biomarker panel with CA19-9, TFPI and TNC-FN III-C was selected. Based on the logistic regression model, a risk score (RS) was determined using RS=0.0816*CA19-9+0.0783*TFPI+0.0229*TNC-FN III-C. An optimal cutoff was decided to be 5.79. For the panel with CA19-9 alone, RS=0.0855*CA19-9, and optimal cutoff was 1.12. The performance of the biomarker panel and its optimal cutoff was tested in two blinded independent validation cohorts.

TABLE 1

Characteristics of study subjects in the early stage TexGen cohort and blinded University of Pittsburgh early stage cohort*.

| Characteristic | Training Set—TEXGEN | | Validation Set—1 University of Pittsburgh cohort | | |
| --- | --- | --- | --- | --- | --- |
| | PDAC (n = 85) | Healthy controls (n = 30) | PDAC (n = 23) | Healthy controls (n = 17) | Chronic pancreatitis (n = 24) |
| Sex | | | | | |
| Male | 46 | 19 | 14 | 6 | 13 |
| Female | 39 | 11 | 9 | 11 | 11 |
| Age, y | | | | | |
| <50 | 4 | 5 | 3 | 3 | 14 |
| 50-60 | 25 | 12 | 6 | 2 | 3 |
| 61-70 | 28 | 10 | 10 | 6 | 6 |
| 71-80 | 22 | 3 | 2 | 2 | 1 |
| >80 | 6 | — | 2 | 4 | — |
| Histology | | | | | |
| Adenocarcinoma | 60 | — | 15 | — | — |
| Infiltrating ductal carcinoma | 24 | — | 8 | — | — |
| Adenocarcinoma spindle cell | 1 | — | 0 | — | — |
| Stage | | | | | |
| I | 25 | — | — | — | — |
| IA | 1 | — | — | — | — |
| IB | 2 | — | — | — | — |
| II | 33 | — | — | — | — |
| IIA | 2 | — | — | — | — |
| IIB | 22 | — | 23 | — | — |
| Alcohol history | | | | | |
| Current | 28 | 13 | 9 | 4 | 8 |
| Former | 18 | 4 | 7 | 5 | 12 |
| Never | 39 | 13 | 6 | 7 | 4 |
| Unknown | — | — | 1 | 1 | 0 |
| Smoking history | | | | | |
| Current | 7 | 0 | 8 | 4 | 12 |
| Former | 44 | 11 | 10 | 6 | 6 |
| Never | 34 | 19 | 5 | 7 | 6 |

TABLE 1-continued

Characteristics of study subjects in the early stage TexGen cohort and blinded University of Pittsburgh early stage cohort*.

| Characteristic | Training Set—TEXGEN | | Validation Set—1 University of Pittsburgh cohort | | |
| --- | --- | --- | --- | --- | --- |
| | PDAC (n = 85) | Healthy controls (n = 30) | PDAC (n = 23) | Healthy controls (n = 17) | Chronic pancreatitis (n = 24) |
| Diabetes history | | | | | |
| Yes | 21 | 5 | 5 | 4 | 6 |
| No | 64 | 25 | 18 | 13 | 18 |
| Site | | | | | |
| Body | 6 | — | 0 | — | — |
| Head | 68 | — | 19 | — | — |
| Pancreas overlapping lesion | 6 | — | 3 | — | — |
| Tail | 2 | — | 0 | — | — |
| Other specified parts | 3 | — | 1 | — | — |
| Stage | | | | | |
| Direct extension | 32 | — | — | — | — |
| Direct extension + lymph node | 16 | — | — | — | — |
| Distant | 3 | — | — | — | — |
| Localized | 25 | — | — | — | — |
| Regional lymph node involvement | 3 | — | — | — | — |
| Unstaged | 6 | — | — | — | — |
| TNM stage | | | | | |
| T1N1Mx | — | — | 2 | — | — |
| T2N1Mx | — | — | 1 | — | — |
| T3N0Mx | — | — | 1 | — | — |
| T3N1Mx | — | — | 14 | — | — |
| T3N1BMx | — | — | 5 | — | — |

* PDAC—pancreatic ductal adenocarcinoma,
endash = not applicable.

Early Stage Cohort 2 Blinded Validation using the Risk Score and Cutoff: Performance of Migration signature panel and corresponding cutoff developed from cohort 1 was validated in early stage PDAC versus chronic pancreatitis cases or healthy controls in cohort 2 (Table 1). For blinded validation analysis, in the comparison of stage IIB (n=23) versus chronic pancreatitis (n=24), the panel of CA19-9 resulted in an AUC of 0.84 (95% CI=0.72 to 0.96), while the three-marker panel provided a slightly higher AUC as 0.86 (95% CI=0.74 to 0.96). The detailed summary of the validation results is provided in Table 7.

Figure 2D:
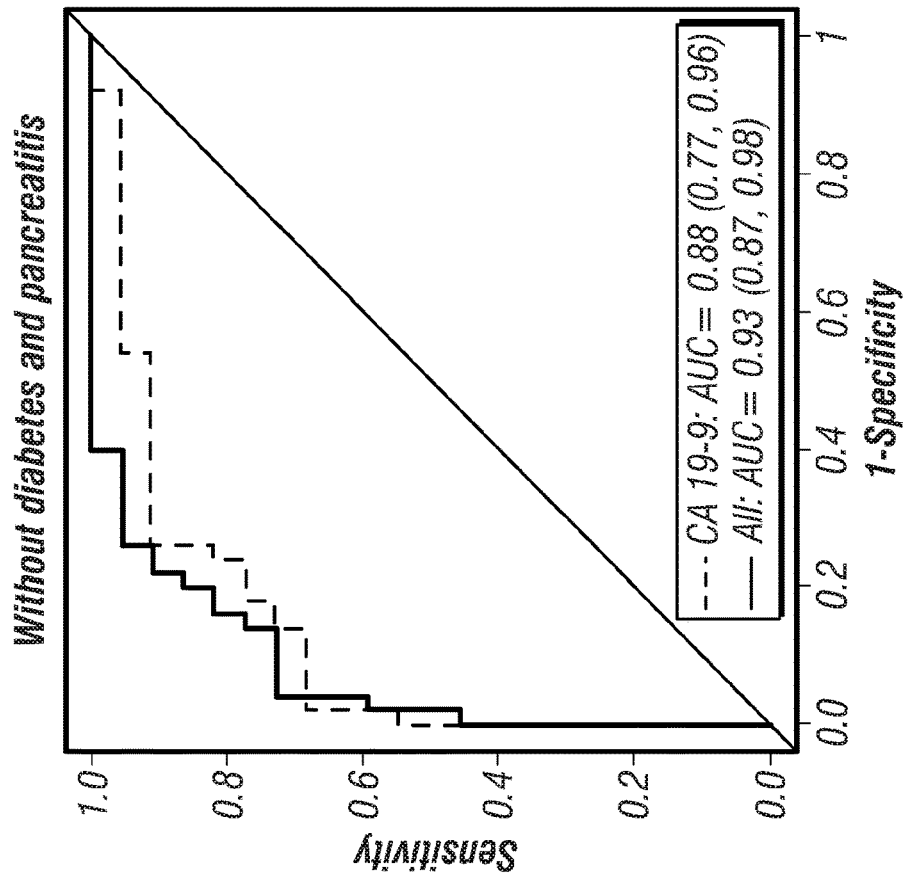

Blinded Validation of the EDRN Reference Set: The performance of migration signature markers was then analyzed in the 252 sample EDRN reference set established by the NCI from multiple institutions using similar SOPs. For discriminating stage IA/IB/IIA cases (n=55) from healthy controls (n=61), compared to CA 19-9 alone (AUC of 0.74 (95% CI=0.64 to 0.84), the combined biomarker panel improved the AUC to 0.79 (95% CI=0.70 to 0.87) using the risk score and determined cutoff (FIG. 2A and Table 3). Corresponding average sensitivity and specificity (accuracy) based on the cutoff improved statistically significant from 0.66 for CA19-9 to 0.77 for the combined biomarker panel (P<0.001). Furthermore, the combined biomarker panel statistically significantly improved CA 19-9 performance in Stage IA/IB/IIA cases (n=55) versus chronic pancreatitis (n=62), with an AUC from 0.69 (95% CI=0.58 to 0.79) to 0.75 (95% CI=0.65 to 0.84) (P=0.045); corresponding accuracy improved from 0.57 to 0.72 (P<0.001). Moreover, by stratifying the cohort to include just the subpopulation free of diabetes and pancreatitis history, an appreciable improvement was observed over the performance of CA 19-9. Within this subpopulation of Stage IA/IB/IIA cases (n=30) versus healthy controls (n=50), the combined model improved CA 19-9 AUC from 0.78 (95% CI=0.66 to 0.89) to 0.87 (95% CI=0.77 to 0.95) (FIG. 2B and Table 3). Corresponding accuracy based on the cutoff determined from cohort 1 improved statistically significantly from 0.65 for CA19-9 to 0.82 for the combined biomarker panel (P<0.001).

Figure 2C:
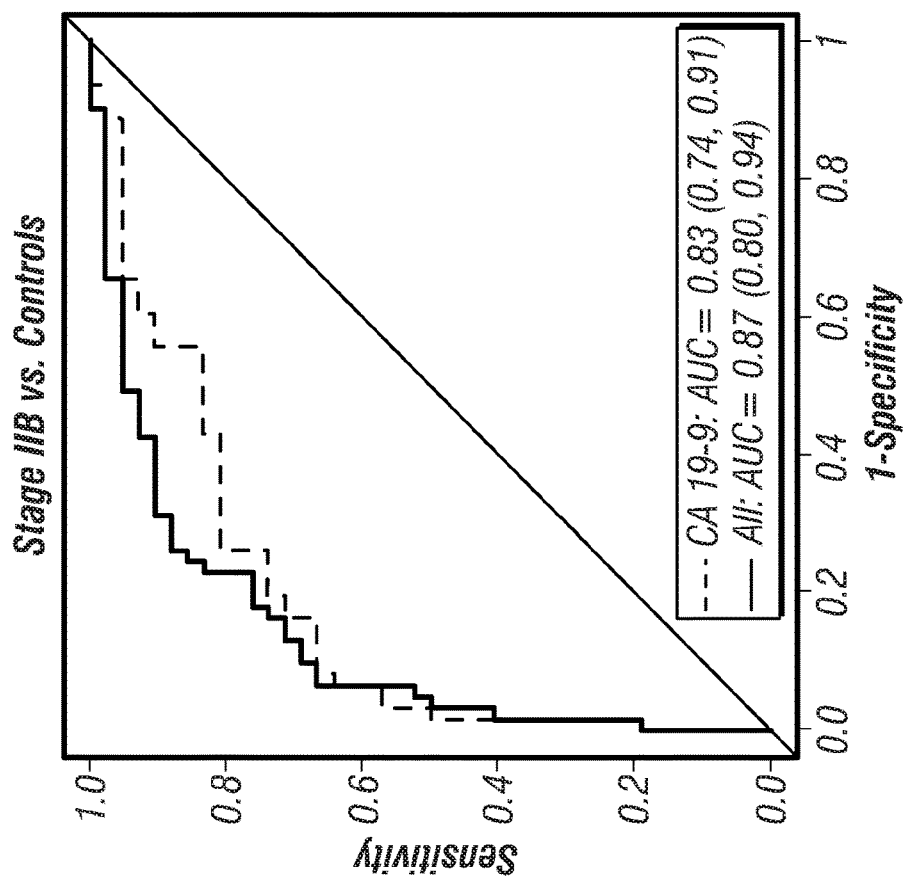

Results from validation of stage IIB PDAC (n=42) versus healthy controls (n=61) indicated that the combined biomarker panel had an AUC of 0.87 (95% CI=0.80 to 0.94) compared to an AUC of 0.83 (95% CI=0.74 to 0.91) for CA 19-9 alone (FIG. 2C and Table 3), with accuracy improving statistically significantly from 0.71 to 0.79 (P=0.03). For stage IIB cases (n=42) versus chronic pancreatitis (n=62), the combined biomarker model improved the AUC of CA 19-9 from 0.77 (95% CI=0.67 to 0.86) to 0.83 (95% CI=0.74 to 0.91) (P=0.05), with corresponding accuracy improving statistically significantly from 0.62 to 0.74 (P=0.009). Among the subcohort free of diabetes and pancreatitis history, based on 22 stage IIB cases and 50 healthy controls, the AUC of the combined model panel was 0.93 (95% CI=0.87 to 0.98), compared to an AUC of 0.88 (95% CI=0.77 to 0.96) for CA19-9 (FIG. 2D and Table 3); corresponding accuracy improved from 0.76 to 0.83. Thus, the combined biomarker model improved gold standard performance, especially for those cases without diabetes or pancreatitis, suggesting that stratification of cohorts might identify individuals for whom AUC values might approach clinical utility.

Figure 3B:
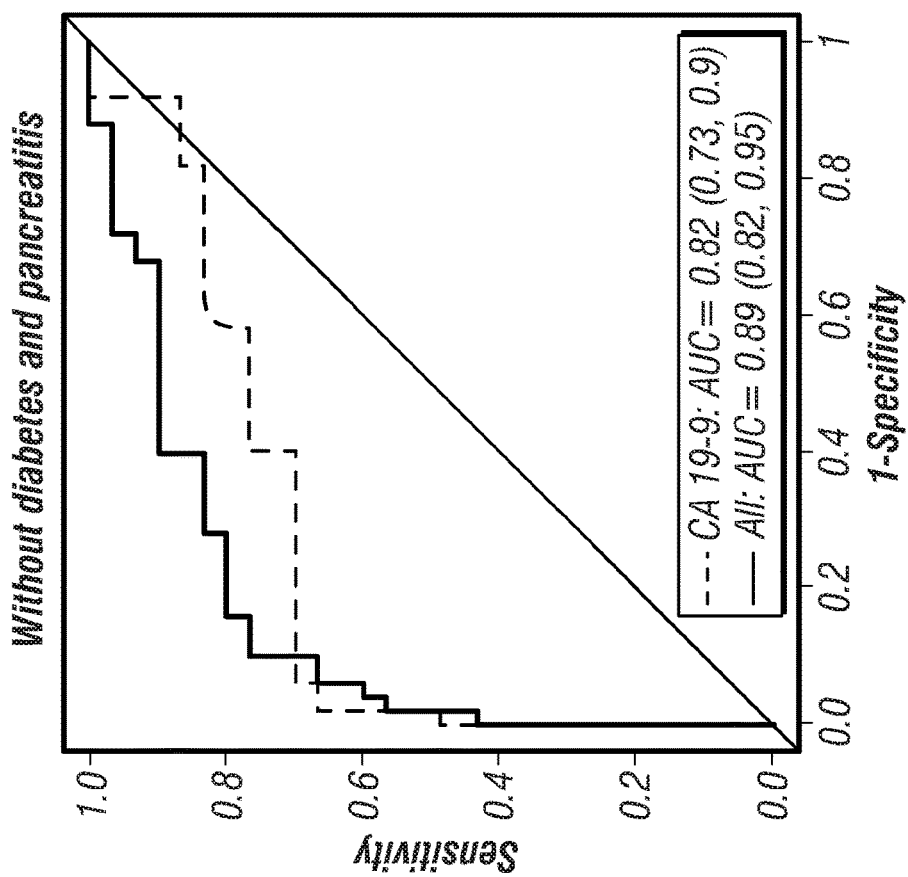
FIGS. 3A-3B: Biomarker panel performance in the EDRN reference set cohort 3. [3A] ROC curves of the biomarker panel model for differentiating all early stage cancer from healthy controls in the EDRN reference set. [3B] ROC curves of the biomarker panel in differentiating all cancer from healthy controls in samples without history of diabetes and chronic pancreatitis. The AUC were calculated, and its 95% CI was estimated using bootstrapping method. P-values are two sided and based on Z-test using bootstrap standard error estimate.
Figure 3A:
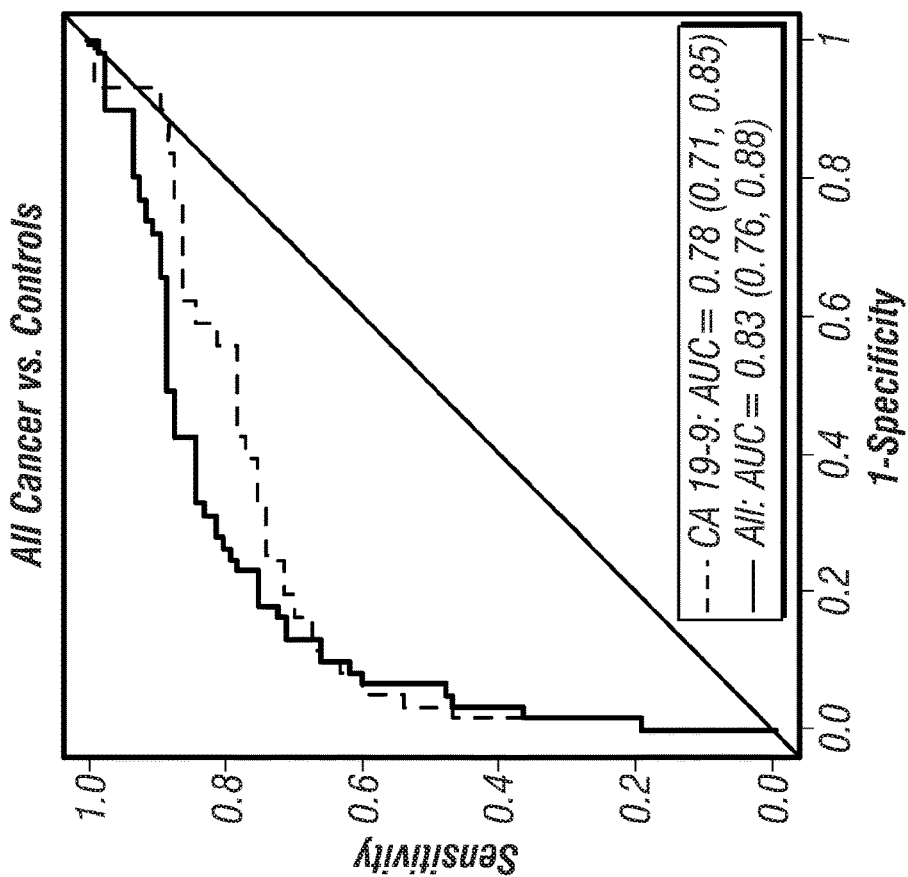
Figure 4:
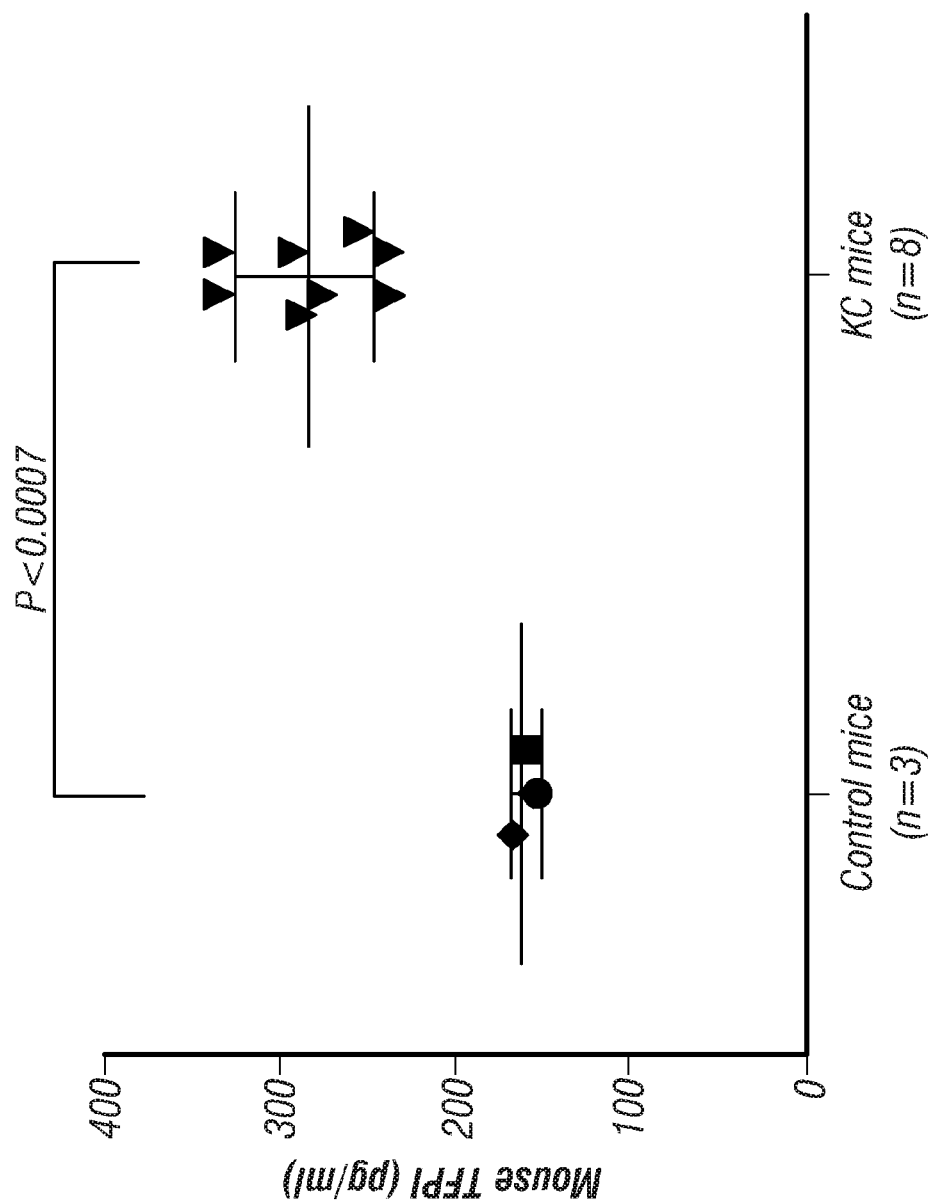
FIG. 4: TFPI ELISA analysis in serum from control mice and KC mice representing PanINs.

The performance of the biomarker panel was next validated based on the combined analysis of all early stage cancer early stage cancer (n=98) versus all healthy controls (n=61). Results indicated a statistically significant improvement in classification performance of the biomarker panel relative to CA19-9. In particular, the AUC for CA 19-9 was 0.78 (95% CI=0.71 to 0.85), which was statistically significantly improved to 0.83 (95% CI=0.76 to 0.89) with the biomarker panel (FIG. 3A and Table 3, P=0.045); corresponding accuracy was also highly statistically significantly improved from 0.68 to 0.78 (P=0.001). Validation of all early stage cancer (n=98) versus chronic pancreatitis (n=62) also indicated statistically significant improvement of CA 19-9 (P=0.01 for AUC values and P<0.001 for accuracy) (Table 3). Analysis of the acute benign biliary obstruction cohorts versus early stage PDAC also showed an improvement in the performance of the combined model over CA 19-9 for all early stage cancer versus benign disease plasma, although not statistically significant (Table 8). Moreover, among the subpopulation free of diabetes and pancreatitis history (n=52 early stage PDAC cases and n=50 healthy controls), compared to CA 19-9 alone AUC of 0.82 (95% CI=0.73 to 0.90), the combined migration signature model resulted in a statistically significantly increased AUC of 0.89 (95% CI=0.82 to 0.95) (P=0.03) (FIG. 3B and Table 3); corresponding accuracy improved statistically significantly from 0.69 to 0.82 (P<0.001).

Validation results in the EDRN reference set clearly demonstrate the value of the addition of the migration signature to CA 19-9 for early detection of PDAC as well as the improvement in performance of the overall panel observed by stratification of the cohort to a subcohort without diabetes and chronic pancreatitis.

TABLE 2

Biomarker panel performance in the TexGen cohort.

| Assay | Stage I/IIA (n = 30) vs Controls (n = 30) | | Stage IIB (n = 22) vs Controls (n = 30) | | Stage II (n = 57) vs Controls (n = 30) | | All Early Stage (n = 85) vs Controls (n = 30) | |
|---|---|---|---|---|---|---|---|---|
| | AUC (95% CI) | P value* | AUC (95% CI) | P value* | AUC (95% CI) | P value* | AUC (95% CI) | P value* |
| CA 19-9 | 0.72 (0.57, 0.86) | 1.00 | 0.87 (0.76, 0.96) | 1.00 | 0.90 (0.82, 0.95) | 1.00 | 0.83 (0.75, 0.90) | 1.00 |
| TFPI | 0.71 (0.57, 0.84) | 0.91 | 0.91 (0.81, 0.98) | 0.58 | 0.86 (0.77, 0.93) | 0.57 | 0.80 (0.71, 0.88) | 0.64 |
| TNC-FNIII-C | 0.54 (0.39, 0.69) | 0.08 | 0.87 (0.77, 0.95) | 0.97 | 0.75 (0.63, 0.85) | 0.04 | 0.68 (0.57, 0.79) | 0.03 |
| TNC-FNIII-C, CA 19-9 | 0.82 (0.71, 0.92) | 0.27 | 0.95 (0.89, 0.99) | 0.14 | 0.92 (0.86, 0.97) | 0.43 | 0.89 (0.83, 0.94) | 0.22 |
| TFPI, CA 19-9 | 0.82 (0.70, 0.91) | 0.29 | 0.98 (0.93, 1.00) | 0.06 | 0.97 (0.94, 0.99) | 0.04 | 0.91 (0.86, 0.96) | 0.06 |
| TNC FNIII-C, TFPI, CA19-9 | 0.84 (0.74, 0.93) | 0.17 | 0.98 (0.95, 1.00) | 0.04 | 0.97 (0.93, 0.99) | 0.03 | 0.92 (0.86, 0.96) | 0.04 |

*P values were two-sided and calculated based on bootstrapping.
AUC = area under the curve;
CI = confidence interval.

TABLE 3

Biomarker panel performance in the EDRN reference set.

| Assay | CA 19-9 | | | | Migration Signature + CA 19-9 | | | | Accuracy P-value* | AUC P-value† |
|---|---|---|---|---|---|---|---|---|---|---|
| | AUC (95% CI) | Sensitivity (95% CI) | Specificity (95% CI) | Accuracy (95% CI) | AUC (95% CI) | Sensitivity (95% CI) | Specificity (95% CI) | Accuracy (95% CI) | | |
| Stage IA/IB/IIA (n = 55) vs. Healthy (n = 61) | 0.74 (0.64, 0.84) | 0.71 (0.58, 0.82) | 0.61 (0.48, 0.74) | 0.66 (0.57, 0.74) | 0.79 (0.70, 0.87) | 0.73 (0.6, 0.84) | 0.82 (0.72, 0.90) | 0.77 (0.70, 0.85) | <0.001 | 0.095 |

TABLE 3-continued

Biomarker panel performance in the EDRN reference set.

| Assay | CA 19-9 | | | | Migration Signature + CA 19-9 | | | | AUC | |
|---|---|---|---|---|---|---|---|---|---|---|
| | AUC (95% CI) | Sensitivity (95% CI) | Specificity (95% CI) | Accuracy (95% CI) | AUC (95% CI) | Sensitivity (95% CI) | Specificity (95% CI) | Accuracy (95% CI) | Accuracy P-value* | P-value† |
| Stage IA/IB/IIA (n = 55) vs. CP (n = 62) | 0.69 (0.58, 0.79) | 0.71 (0.58, 0.82) | 0.44 (0.31, 0.57) | 0.57 (0.48, 0.66) | 0.75 (0.65, 0.84) | 0.73 (0.62, 0.84) | 0.71 (0.60, 0.81) | 0.72 (0.64, 0.80) | <0.001 | 0.045 |
| Without history of diabetes and pancreatitis | | | | | | | | | | |
| Stage IA/IB/IIA (n = 30) vs Healthy (n = 50) | 0.78 (0.66, 0.89) | 0.7 (0.53, 0.87) | 0.6 (0.46, 0.72) | 0.65 (0.55, 0.75) | 0.87 (0.77, 0.95) | 0.8 (0.63, 0.93) | 0.84 (0.74, 0.94) | 0.82 (0.73, 0.91) | <0.001 | 0.07 |
| Stage IIB (n = 42) vs. Healthy (n = 61) | 0.83 (0.74, 0.91) | 0.81 (0.69, 0.93) | 0.61 (0.48, 0.72) | 0.71 (0.62, 0.79) | 0.87 (0.80, 0.94) | 0.76 (0.64, 0.88) | 0.82 (0.72, 0.90) | 0.79 (0.71, 0.87) | 0.03 | 0.18 |
| Stage IIB (n = 42) vs. CP (n = 62) | 0.77 (0.67, 0.86) | 0.81 (0.69, 0.93) | 0.44 (0.32, 0.57) | 0.62 (0.54, 0.71) | 0.83 (0.74, 0.91) | 0.76 (0.62, 0.88) | 0.71 (0.60, 0.82) | 0.74 (0.65, 0.82) | 0.009 | 0.05 |
| Without history of diabetes and pancreatitis | | | | | | | | | | |
| Stage IIB (n = 22) vs. Healthy (n = 50) | 0.88 (0.77, 0.96) | 0.91 (0.77, 1) | 0.6 (0.46, 0.74) | 0.76 (0.66, 0.83) | 0.93 (0.87, 0.98) | 0.82 (0.64, 0.96) | 0.84 (0.74, 0.94) | 0.83 (0.73, 0.92) | 0.08 | 0.22 |
| All Cancer (n = 98) vs. Healthy (n = 61) | 0.78 (0.71, 0.85) | 0.76 (0.66, 0.84) | 0.61 (0.48, 0.72) | 0.68 (0.60, 0.75) | 0.83 (0.76, 0.89) | 0.75 (0.65, 0.83) | 0.82 (0.71, 0.90) | 0.78 (0.72, 0.84) | 0.001 | 0.045 |
| All Cancer (n = 98) vs. CP (n = 62) | 0.73 (0.64, 0.80) | 0.76 (0.66, 0.84) | 0.44 (0.32, 0.55) | 0.60 (0.52, 0.67) | 0.78 (0.71, 0.85) | 0.75 (0.65, 0.83) | 0.71 (0.60, 0.82) | 0.73 (0.65, 0.79) | <0.001 | 0.01 |
| Without history of diabetes and pancreatitis | | | | | | | | | | |
| All Cancer (n = 52) vs. Healthy (n = 50) | 0.82 (0.73, 0.90) | 0.79 (0.67, 0.89) | 0.6 (0.46, 0.74) | 0.69 (0.61, 0.77) | 0.89 (0.82, 0.95) | 0.81 (0.69, 0.90) | 0.84 (0.72, 0.94) | 0.82 (0.75, 0.89) | <0.001 | 0.03 |

*Two-sided P-value based on Z-test for equivalence in accuracy between CA 19-9 and migration signature + CA 19-9, using bootstrap standard error estimate.
AUC = area under the curve;
CP = chronic pancreatitis;
CI = confidence interval.

TABLE 4

Biomarker panel performance in the EDRN reference set after adding age and diabetes status (not included for subcohort free of diabetes and chronic pancreatitis) into the risk model, based on model developed using EDRN reference set sample*.

| Assay | CA-19-9 | | | Migration signature + CA19-9 | | |
|---|---|---|---|---|---|---|
| | AUC (95% CI) | Optimal sensitivity | Optimal specificity | AUC (95% CI) | Optimal sensitivity | Optimal specificity |
| Full cohort after adjusting for age and diabetes status | | | | | | |
| Stage IA/IB/IIA (n = 54) vs. Healthy (n = 56) | 0.85 (0.77-0.92) | 0.82 | 0.79 | 0.86 (0.79-0.93) | 0.76 | 0.84 |
| Stage IA/IB/IIA (n = 54) vs. Benign (n = 31) | 0.69 (0.60-0.82) | 0.39 | 0.90 | 0.71 (0.64-0.84) | 0.48 | 0.87 |
| Sub cohort without history of diabetes and pancreatitis after adjusting for age | | | | | | |
| Stage IA/IB/IIA (n = 30) vs. Healthy (n = 50) | 0.89 (0.81-0.96) | 0.80 | 0.90 | 0.90 (0.83-0.98) | 0.80 | 0.94 |
| Stage IA/IB/IIA (n = 30) vs. Benign (n = 21) | 0.65 (0.53-0.82) | 0.77 | 0.52 | 0.71 (0.60-0.88) | 0.93 | 0.43 |
| Full cohort after adjusting for age and diabetes status | | | | | | |
| Stage IIB (n = 38) vs. Healthy (n = 56) | 0.86 (0.75-0.95) | 0.71 | 0.91 | 0.88 (0.81-0.97) | 0.84 | 0.79 |
| Stage IIB (n = 38) vs Benign (n = 31) | 0.64 (0.54-0.79) | 0.32 | 0.97 | 0.74 (0.67-0.87) | 0.82 | 0.55 |
| Sub cohort without history of diabetes and pancreatitis after adjusting for age | | | | | | |
| Stage IIB (n = 22) vs. Healthy (n = 50) | 0.89 (0.79-0.97) | 0.86 | 0.80 | 0.93 (0.87-1.00) | 0.91 | 0.86 |
| Stage IIB (n = 22) vs Benign (n = 21) | 0.59 (0.49-0.81) | 0.82 | 0.48 | 0.80 (0.67-0.94) | 0.77 | 0.71 |
| Full cohort after adjusting for age and diabetes status | | | | | | |
| All Cancer (n = 93) vs. Healthy (n = 56) | 0.85 (0.78-0.91) | 0.73 | 0.88 | 0.86 (0.79-0.93) | 0.81 | 0.8 |
| All Cancer (n = 93) vs. Benign (n = 31) | 0.66 (0.58-0.77) | 0.58 | 0.68 | 0.71 (0.61-0.82) | 0.59 | 0.74 |

TABLE 4-continued

Biomarker panel performance in the EDRN reference set after adding age and diabetes status (not included for subcohort free of diabetes and chronic pancreatitis) into the risk model, based on model developed using EDRN reference set sample*.

| Assay | CA-19-9 | | | Migration signature + CA19-9 | | |
|---|---|---|---|---|---|---|
| | AUC (95% CI) | Optimal sensitivity | Optimal specificity | AUC (95% CI) | Optimal sensitivity | Optimal specificity |
| Sub cohort without history of diabetes and pancreatitis after adjusting for age | | | | | | |
| All Cancer (n = 52) vs. Healthy (n = 50) | 0.88 (0.80-0.93) | 0.69 | 0.98 | 0.90 (0.85-0.97) | 0.75 | 0.96 |
| All Cancer (n = 52) vs. Benign (n = 21) | 0.62 (0.53-0.80) | 0.79 | 0.52 | 0.74 (0.64-0.87) | 0.73 | 0.67 |

*Benign refers to acute benign biliary obstruction.
AUC = area under the curve;
CI = confidence interval.

TABLE 5

Characteristics of study population used for CLIA validation.

| Characteristic | No. of PDAC cases (n = 20) | No. of Healthy controls (n = 20) |
|---|---|---|
| Sex | | |
| Male | 12 | 10 |
| Female | 8 | 10 |
| Age, y* | | |
| <50 | 5 | 9 |
| 50-60 | 7 | 5 |
| 61-70 | 6 | 4 |
| 71-80 | 2 | 1 |
| Histology | | |
| Adenocarcinoma, Stage IV | 20 | N/A |
| Alcohol history | | |
| Current | 9 | n/a |
| Former | 3 | n/a |
| Never | 8 | n/a |
| Smoking history | | |
| Current | 2 | n/a |
| Former | 8 | n/a |
| Never | 10 | n/a |
| Diabetes history | | |
| Yes | 5 | n/a |
| No | 15 | n/a |
| Site | | |
| Body | 4 | N/A |
| Head | 11 | N/A |
| Pancreas overlapping lesion | 1 | N/A |
| Tail | 3 | N/A |
| Other specified parts | 1 | N/A |
| Stage | | |
| Direct extension | 2 | N/A |
| Distant | 18 | N/A |

TABLE 6

Biomarker performance of the marker as analyzed in both biomarker discovery lab as well as in CLIA laboratory*.

| Marker | MDACC Results | | | CLIA Results | | |
|---|---|---|---|---|---|---|
| | AUC (95% CI) | Optimal Sensitivity | Optimal Specificity | AUC (95% CI) | Optimal Sensitivity | Optimal Specificity |
| TFPI | 0.80 (0.65-0.94) | 0.70 | 0.80 | 0.78 (0.64-0.93) | 0.75 | 0.75 |
| CA 19-9 | 0.71 (0.52-0.90) | 0.65 | 1.00 | 0.72 (0.54-0.90) | 0.65 | 1.00 |
| TNC-FN III-C | 0.59 (0.40-0.78) | 0.60 | 0.70 | 0.68 (0.51-0.85) | 0.55 | 0.80 |
| TNC-FN III-C + TFPI | 0.80 (0.66-0.94) | 0.70 | 0.85 | 0.83 (0.69-0.97) | 0.85 | 0.80 |
| TNC-FN III-C + CA19-9 | 0.74 (0.56-0.92) | 0.65 | 1.00 | 0.82 (0.65-0.98) | 0.80 | 0.90 |
| TFPI + CA 19-9 | 0.92 (0.82-1.00) | 0.85 | 0.85 | 0.92 (0.82-1.00) | 0.85 | 0.85 |
| TNC-FN III-C + TFPI + CA19-9 | 0.92 (0.82-1.00) | 0.85 | 0.85 | 0.92 (0.82-1.00) | 0.95 | 0.85 |

TABLE 7

Validation of the biomarker model in University of Pittsburgh cohort.

| | CA-19-9 | | | | Migration Signature + CA-19-9 | | | | | |
| --- | --- | --- | --- | --- | --- | --- | --- | --- | --- | --- |
| Assay | AUC (95% CI) | Sensitivity (95% CI) | Specificity (95% CI) | Accuracy (95% CI) | AUC (95% CI) | Sensitivity (95% CI) | Specificity (95% CI) | Accuracy (95% CI) | Accuracy P value* | AUC P value† |
| Stage IIB (n = 23) vs Controls (n = 17) | 0.86 (0.72-0.96) | 0.83 (0.65-0.96) | 0.76 (0.53-0.94) | 0.80 (0.68-0.90) | 0.85 (0.73-0.96) | 0.83 (0.70-0.96) | 0.76 (0.59-0.94) | 0.80 (0.70-0.90) | 1.00 | 0.95 |
| Stage IIB (n = 23) vs CP (n = 24) | 0.84 (0.72-0.96) | 0.83 (0.65-0.96) | 0.75 (0.56-0.88) | 0.79 (0.66-0.89) | 0.86 (0.74-0.96) | 0.83 (0.67-0.96) | 0.88 (0.73-1.00) | 0.85 (0.74-0.94) | 0.23 | 0.87 |
| Stage IIB (n = 23) vs Controls + CP (n = 41) | 0.85 (0.72-0.96) | 0.83 (0.65-0.96) | 0.74 (0.61-0.86) | 0.77 (0.67-0.86) | 0.86 (0.75-0.95) | 0.83 (0.65-0.96) | 0.82 (0.72-0.92) | 0.82 (0.73-0.90) | 0.31 | 0.93 |

TABLE 8

Biomarker panel model performance in EDRN reference set cohort in differentiating stage IA/IB/IIA, stage IIB and all cancer samples from acute benign biliary obstruction samples.

| | CA 19-9 | | | | Migration Signature + CA 19-9 | | | | | |
| --- | --- | --- | --- | --- | --- | --- | --- | --- | --- | --- |
| Assay | AUC (95% CI) | Sensitivity (95% CI) | Specificity (95% CI) | Accuracy (95% CI) | AUC (95% CI) | Sensitivity (95% CI) | Specificity (95% CI) | Accuracy (95% CI) | Accuracy P-value* | AUC P-value† |
| Stage IA/IB/IIA (n = 55) vs. Benign (n = 31) | 0.54 (0.41-0.66) | 0.71 (0.58-0.84) | 0.26 (0.13-0.42) | 0.48 (0.38-0.59) | 0.57 (0.45-0.69) | 0.73 (0.62-0.84) | 0.36 (0.19-0.55) | 0.54 (0.45-0.65) | 0.27 | 0.32 |
| Stage IIB (n = 42) vs. Benign (n = 31) | 0.58 (0.44-0.70) | 0.81 (0.69-0.93) | 0.26 (0.12-0.42) | 0.53 (0.44-0.63) | 0.61 (0.48-0.74) | 0.76 (0.64-0.88) | 0.36 (0.19-0.52) | 0.56 (0.45-0.67) | 0.65 | 0.25 |
| All Cancer (n = 98) vs. Benign (n = 31) | 0.56 (0.44-0.67) | 0.76 (0.66-0.84) | 0.26 (0.13-0.42) | 0.51 (0.42-0.60) | 0.58 (0.47-0.69) | 0.75 (0.65-0.83) | 0.36 (0.19-0.52) | 0.55 (0.46-0.64) | 0.38 | 0.22 |
| Without history of diabetes and pancreatitis | | | | | | | | | | |
| Stage IA/IB/IIA (n = 30) vs. Benign (n = 21) | 0.61 (0.45-0.75) | 0.7 (0.54-0.87) | 0.33 (0.14-0.53) | 0.52 (0.38-0.64) | 0.62 (0.46-0.77) | 0.8 (0.63-0.93) | 0.38 (0.19-0.62) | 0.59 (0.46-0.72) | 0.28 | 0.75 |
| Stage IIB (n = 22) vs. Benign (n = 21) | 0.65 (0.47-0.81) | 0.91 (0.77-1.00) | 0.33 (0.14-0.53) | 0.62 (0.50-0.74) | 0.65 (0.49-0.81) | 0.82 (0.64-0.96) | 0.38 (0.19-0.57) | 0.6 (0.48-0.72) | 0.75 | 0.96 |
| All Cancer (n = 52) vs. Benign (n = 21) | 0.62 (0.49-0.76) | 0.79 (0.67-0.89) | 0.33 (0.14-0.52) | 0.56 (0.45-0.67) | 0.63 (0.49-0.78) | 0.81 (0.69-0.90) | 0.38 (0.19-0.62) | 0.59 (0.48-0.72) | 0.62 | 0.79 |

TABLE 9

Logistic regression analysis in the EDRN reference set in the full cohort and in the subcohort without the history of diabetes and pancreatitis.

| Sample and Coefficient | Full Cohort | | | No History of Diabetes and Pancreatitis | | |
| --- | --- | --- | --- | --- | --- | --- |
| | Estimate | 95% CI | P-value* | Estimate | 95% CI | P-value* |
| All Cancer vs Healthy | | | | | | |
| Intercept | -4.889 | (-8.026, -1.751) | 0.002 | -9.278 | (-14.175, -4.381) | <0.001 |
| CA19-9 | 0.022 | (0.005, 0.039) | 0.01 | 0.065 | (0.025, 0.105) | 0.001 |
| TFPI | 0.050 | (0.009, 0.091) | 0.02 | 0.079 | (0.016, 0.142) | 0.01 |
| TNC-FNIII-C | 0.007 | (-0.004, 0.018) | 0.22 | 0.006 | (-0.006, 0.019) | 0.33 |
| AGE | 0.034 | (-0.008, 0.075) | 0.11 | 0.068 | (0.008, 0.128) | 0.03 |
| Diabetes | 1.165 | (0.084, 2.247) | 0.03 | — | — | — |

TABLE 9-continued

Logistic regression analysis in the EDRN reference set in the full cohort and in the subcohort without the history of diabetes and pancreatitis.

| Sample and Coefficient | Full Cohort | | | No History of Diabetes and Pancreatitis | | |
|---|---|---|---|---|---|---|
| | Estimate | 95% CI | P-value* | Estimate | 95% CI | P-value* |
| Stage IA/IB/IIA vs Health | | | | | | |
| Intercept | −5.784 | (−9.537, −2.031) | 0.003 | −10.972 | (−17.100, −4.844) | <0.001 |
| CA19-9 | 0.015 | (0.002, 0.029) | 0.02 | 0.067 | (0.021, 0.114) | 0.004 |
| TFPI | 0.039 | (−0.012, 0.090) | 0.14 | 0.051 | (−0.034, 0.136) | 0.24 |
| TNC-FNIII-C | 0.008 | (−0.004, 0.019) | 0.20 | 0.007 | (−0.006, 0.020) | 0.29 |
| AGE | 0.046 | (−0.002, 0.094) | 0.06 | 0.097 | (0.023, 0.171) | 0.01 |
| Diabetes | 1.299 | (0.144, 2.454) | 0.03 | — | — | — |
| Stage IIB vs Healthy | | | | | | |
| Intercept | −6.603 | (−11.092, −2.113) | 0.004 | −9.533 | (−17.170, −1.895) | 0.01 |

TABLE 10

Individual Biomarker performance under different combinations in the EDRN reference set in differentiating all cancer, stage IA/IB/IIA and stage IIB samples from healthy controls, chronic pancreatitis and acute benign biliary obstruction samples.

| Assay | AUC (95% CI) | | | | | |
|---|---|---|---|---|---|---|
| | CA 19-9 | TFPI | TNC-C | CA19-9 + TFPI | CA19-9 + TNC | All |
| All Cancer (n = 98) vs. Healthy (n = 61) | 0.78 (0.71-0.85) | 0.66 (0.57-0.74) | 0.62 (0.47-0.71) | 0.81 (0.74-0.88) | 0.81 (0.74-0.87) | 0.82 (0.75-0.89) |
| All Cancer (n = 98) vs. CP (n = 62) | 0.73 (0.65-0.80) | 0.65 (0.56-0.74) | 0.60 (0.50-0.68) | 0.77 (0.69-0.85) | 0.77 (0.69-0.83) | 0.79 (0.72-0.86) |
| All Cancer (n = 98) vs. Benign (n = 31) | 0.56 (0.45-0.67) | 0.54 (0.45-0.64) | 0.49 (0.40-0.64) | 0.55 (0.48-0.68) | 0.57 (0.49-0.71) | 0.61 (0.53-0.73) |
| Stage IA/IB/IIA (n = 55) vs. Healthy (n = 61) | 0.74 (0.63-0.84) | 0.62 (0.52-0.71) | 0.63 (0.48-0.74) | 0.77 (0.67-0.85) | 0.80 (0.69-0.88) | 0.79 (0.70-0.88) |
| Stage IA/IB/IIA (n = 55) vs. CP (n = 62) | 0.69 (0.58, 0.79) | 0.61 (0.52-0.71) | 0.60 (0.51-0.70) | 0.72 (0.63-0.82) | 0.75 (0.66-0.84) | 0.75 (0.68-0.85) |
| Stage IA/IB/IIA (n = 55) vs. Benign (n = 31) | 0.54 (0.43-0.65) | 0.49 (0.43-0.64) | 0.48 (0.39-0.66) | 0.54 (0.46-0.69) | 0.57 (0.46-0.73) | 0.58 (0.50-0.74) |
| Stage IIB (n = 42) vs. Healthy (n = 61) | 0.83 (0.74-0.91) | 0.72 (0.62-0.83) | 0.61 (0.46-0.72) | 0.85 (0.75-0.94) | 0.84 (0.75-0.92) | 0.85 (0.75-0.94) |
| Stage IIB (n = 42) vs. CP (n = 62) | 0.77 (0.67-0.85) | 0.71 (0.61-0.80) | 0.59 (0.49-0.70) | 0.82 (0.73-0.91) | 0.79 (0.69-0.88) | 0.83 (0.75-0.91) |
| Stage IIB (n = 42) vs Benign (n = 31) | 0.58 (0.38-0.70) | 0.61 (0.49-0.73) | 0.50 (0.39-0.66) | 0.62 (0.49-0.75) | 0.57 (0.46-0.74) | 0.64 (0.54-0.78) |
| After adjusting for age and diabetes status | | | | | | |
| All Cancer (n = 93) vs. Healthy (n = 56) | 0.85 (0.78-0.91) | 0.77 (0.7-0.85) | 0.70 (0.63-0.8) | 0.87 (0.79-0.93) | 0.86 (0.78-0.92) | 0.86 (0.79-0.93) |
| All Cancer (n = 93) vs. CP (n = 60) | 0.86 (0.80-0.92) | 0.77 (0.71-0.86) | 0.76 (0.69-0.85) | 0.86 (0.8-0.92) | 0.85 (0.81-0.92) | 0.86 (0.81-0.93) |
| All Cancer (n = 93) vs. Benign (n = 31) | 0.66 (0.58-0.77) | 0.66 (0.58, 0.77) | 0.65 (0.55-0.76) | 0.67 (0.59-0.79) | 0.7 (0.59-0.80) | 0.71 (0.61-0.82) |
| Stage IA/IB/IIA (n = 54) vs. Healthy (n = 56) | 0.85 (0.77-0.92) | 0.75 (0.65-0.84) | 0.72 (0.64-0.82) | 0.85 (0.78-0.93) | 0.85 (0.79-0.93) | 0.86 (0.79-0.93) |
| Stage IA/IB/IIA (n = 54) vs. CP (n = 60) | 0.86 (0.79-0.93) | 0.76 (0.68-0.86) | 0.76 (0.69-0.86) | 0.85 (0.79-0.93) | 0.86 (0.79-0.93) | 0.86 (0.79-0.94) |
| Stage IA/IB/IIA (n = 54) vs. Benign (n = 31) | 0.69 (0.60-0.82) | 0.66 (0.57-0.78) | 0.66 (0.57-0.79) | 0.69 (0.61-0.82) | 0.72 (0.62-0.83) | 0.71 (0.64-0.84) |
| Stage IIB (n = 38) vs. Healthy (n = 56) | 0.86 (0.75-0.95) | 0.83 (0.75-0.92) | 0.7 (0.60-0.81) | 0.88 (0.8-0.97) | 0.86 (0.76-0.95) | 0.88 (0.81-0.97) |

TABLE 10-continued

Individual Biomarker performance under different combinations in the EDRN reference set in differentiating all cancer, stage IA/IB/IIA and stage IIB samples from healthy controls, chronic pancreatitis and acute benign biliary obstruction samples.

| | AUC (95% CI) | | | | | |
|---|---|---|---|---|---|---|
| Assay | CA 19-9 | TFPI | TNC-C | CA19-9 + TFPI | CA19-9 + TNC | All |
| Stage IIB (n = 38) vs. CP (n = 60) | 0.88 (0.82-0.94) | 0.82 (0.75-0.91) | 0.78 (0.69-0.87) | 0.88 (0.82-0.96) | 0.88 (0.82-0.94) | 0.88 (0.83-0.96) |
| Stage IIB (n = 38) vs Benign (n = 31) | 0.64 (0.54-0.79) | 0.71 (0.62-0.83) | 0.67 (0.56-0.8) | 0.72 (0.62-0.84) | 0.70 (0.60-0.83) | 0.74 (0.67-0.87) |

AUC, area under the curve.
CP, chronic pancreatitis.
Benign-acute benign biliary obstruction.
Migration signature refers to the combination of both TFPI and TNC-FNIIIC.
Models were developed with or without addition of age and diabetes status as predictors.

TABLE 11

Individual Biomarker performance under different combinations in the EDRN reference set in differentiating stage IA/IB/IIA and stage IIB samples from healthy controls, chronic pancreatitis and acute benign biliary obstruction samples without history of diabetes or chronic pancreatitis.

| | AUC (95% CI) | | | | | |
|---|---|---|---|---|---|---|
| Assay | CA19-9 | TFPI | TNC-C | CA19-9 + TFPI | CA 19-9 + TNC | All |
| All Cancer (n = 52) vs. Healthy (n = 50) | 0.82 (0.73-0.91) | 0.77 (0.68-0.85) | 0.65 (0.40-0.76) | 0.89 (0.82-0.95) | 0.85 (0.78-0.93) | 0.89 (0.83-0.96) |
| All Cancer (n = 52) vs. Benign (n = 21) | 0.62 (0.40-0.76) | 0.58 (0.46-0.72) | 0.57 (0.44-0.72) | 0.58 (0.49-0.78) | 0.68 (0.55-0.81) | 0.70 (0.58-0.84) |
| Stage IA/IB/IIA (n = 30) vs. Healthy (n = 50) | 0.78 (0.63-0.90) | 0.71 (0.58-0.83) | 0.67 (0.46-0.798) | 0.86 (0.74-0.94) | 0.82 (0.71-0.94) | 0.86 (0.77-0.95) |
| Stage IA/IB/IIA (n = 30) vs. Benign (n = 21) | 0.61 (0.45-0.75) | 0.52 (0.42-0.69) | 0.54 (0.41, 0.70) | 0.58 (0.47-0.78) | 0.66 (0.53-0.81) | 0.66 (0.57-0.82) |
| Stage IIB (n = 22) vs. Healthy (n = 50) | 0.88 (0.76-0.97) | 0.85 (0.71-0.94) | 0.62 (0.37-0.76) | 0.93 (0.85-1.0) | 0.88 (0.78-0.97) | 0.93 (0.86-1.0) |
| Stage IIB (n = 22) vs Benign (n = 21) | 0.65 (0.28-0.81) | 0.65 (0.49-0.81) | 0.62 (0.49-0.79) | 0.66 (0.52-0.83) | 0.71 (0.57-0.86) | 0.76 (0.64-0.92) |
| After adjusting for age | | | | | | |
| All Cancer (n = 52) vs. Healthy (n = 50) | 0.88 (0.80-0.93) | 0.79 (0.71-0.88) | 0.73 (0.64-0.83) | 0.90 (0.84-0.96) | 0.88 (0.82-0.94) | 0.90 (0.85-0.97) |
| All Cancer (n = 52) vs. Benign (n = 21) | 0.62 (0.53-0.80) | 0.63 (0.52-0.77) | 0.65 (0.53-0.79) | 0.63 (0.55-0.82) | 0.72 (0.62-0.86) | 0.74 (0.64-0.87) |
| Stage IA/IB/IIA (n = 30) vs. Healthy (n = 50) | 0.89 (0.81-0.96) | 0.74 (0.64-0.86) | 0.74 (0.63-0.85) | 0.90 (0.81-0.97) | 0.89 (0.82-0.97) | 0.90 (0.83-0.98) |
| Stage IA/IB/IIA (n = 30) vs. Benign (n = 21) | 0.65 (0.53-0.82) | 0.61 (0.49-0.78) | 0.64 (0.51-0.82) | 0.64 (0.54-0.84) | 0.71 (0.59-0.87) | 0.71 (0.60-0.88) |
| Stage IIB (n = 22) vs. Healthy (n = 50) | 0.89 (0.79-0.97) | 0.87 (0.77-0.96) | 0.72 (0.50-0.84) | 0.93 (0.85-1.0) | 0.88 (0.79-0.97) | 0.93 (0.87-1.0) |
| Stage IIB (n = 22) vs Benign (n = 21) | 0.59 (0.49-0.81) | 0.70 (0.56-0.85) | 0.67 (0.54-0.84) | 0.71 (0.57-0.87) | 0.75 (0.61-0.9) | 0.80 (0.67-0.94) |

AUC area under the curve.
CP, chronic pancreatitis.
Benign-acute benign biliary obstruction.
Migration signature refers to the combination of both TFPI and TNC-FNIIIC.
Models were developed with or without addition of age as predictors.

Evaluation of Additional Risk Factors including Age and Diabetes Status: Based on the EDRN reference set data, the performance of the three markers combined with age and diabetes status was further explored based on results from the EDRN reference set. For this analysis, a logistic regression model was refitted to each case/control group including all three markers, plus age, and diabetes status among the full cohort or age only among the subcohort free of diabetes and chronic pancreatitis. Results for the model performance are presented in Table 4. In particular, among the subcohort free of diabetes and chronic pancreatitis, the risk score developed achieved an AUC of 0.90, 0.93, and 0.90 respectively for discriminating stage IA/IB/IIA, stage IIB, or all early stage cancer from healthy controls. Results for the logistic regression model for early stage cancer and healthy controls are presented in Table 3.

In conclusion, the present studies document the role of TFPI and TNC-FN III-C to discriminate early stage PDAC cases from healthy controls as well as their potential as biomarker to improve CA 19-9 performance for PDAC early detection. Using the migration signature and CA 19-9 marker panel developed in cohort 3 representing the EDRN reference set, a statistically significant improvement in AUC was observed that distinguished all early stage cancer from both healthy controls and chronic pancreatitis. Moreover, based on the optimal cutoffs developed in cohort 1, dramatic improvements in the accuracy over CA 19-9 were observed in cohort 3 for distinguishing all early stage cancer from healthy controls and chronic pancreatitis. Results indicate that the combined marker panel model could provide a more accurate test with high sensitivities and specificities for early detection of PDAC when used in combination with CA 19-9, and that the panel is independent of diabetes and chronic pancreatitis risk. Furthermore, when all cases of early PDAC were combined in the EDRN cohort, results were strengthened demonstrating statistical significance for multiple combinations of cases and controls.

Example 2—Materials and Methods

Clinical Cohorts: A plasma cohort of 20 late stage IV PDAC and 20 normal controls was used for CLIA laboratory validation studies. Early Stage Pre-Validation Cohort 1 contained 115 samples, including 85 early stage PDAC cases: Stage I (n=28), Stage II (n=57), and 30 GI screening controls obtained from the TexGen repository, a Texas Medical Center consortium. Early Stage Blinded Validation Cohort 2 from the University of Pittsburgh included 64 samples: Stage IIB (n=23), chronic pancreatitis (n=24), and GI controls (n=17). Early Stage Blinded Validation Cohort 3 is the NCI Early Detection Research Network (EDRN) pancreatic cancer reference set of 252 plasma samples, including 98 early stage PDAC cases: Stage IA (n=7), IB (n=8), II (n=1), IIA (n=40), IIB (n=42), 62 chronic pancreatitis controls, 31 acute biliary obstruction controls and 61 healthy controls (Haab et al., 2015). Study protocols were approved by the institutional review board, and all patients gave written informed consent.

ELISA Assays: ELISA assays for TFPI were performed as previously described (Balasenthil et al., 2011). Plasma levels of Tenascin C [FN III-C] were determined using a Human Tenascin-C (FN III-C) ELISA kit (IBL-America, Minneapolis, Minn.), which detects FN III-C domain by sandwich ELISA. Samples were diluted 50 fold and then incubated in ELISA plates pre-coated with anti-human tenascin-C (19C4MS) Mouse IgG MAb specific to FN III-C domain at 37° C. for 60 minutes. Briefly after washing the wells 7 times with wash buffer, a horseradish-peroxidase conjugated anti-human tenascin C (4F10TT) Ab was added and incubated at 4° C. for 30 minutes. Wells were washed with buffer (9 times), the chromogen solution was added and incubated for 30 minutes in the dark at room temperature. The reaction was stopped and read within 30 minutes using an ELISA plate reader (Spectramax Plus$^{384}$, Spectramax Plus$^{190}$, Molecular Devices and iMark Microplate Readers, BioRad). Results are mean absorbance of duplicate wells. CA 19-9 ELISAs were performed as previously described and reported in which this CA 19-9 ELISA assay, with two other CA 19-9 assays, showed similar performance ((Balasenthil et al., 2011; Haab et al., 2015).

Statistical Methods: All statistical tests were two-sided and P value of less than 0.05 was considered statistically significant.

CLIA Analysis: A logistic regression model was used to distinguish PDAC from healthy controls. To determine the threshold of the risk score for optimal sensitivity and specificity, the point with shortest distance value form the point $(0,1)$ $[(1-\text{sensitivity})^2+(1-\text{specificity})^2]$ was calculated (DeLong et al., 1998). All statistical analyses were performed using Stata 13.1 software (Stata Corporation).

Analysis of Early Stage Cohort 1 (TexGen Cohort): A logistic regression model was used to analyze the performance of markers and identify collective performance of the panel relative to CA 19-9. ROC curves and AUCs were calculated and their 95% percentile bootstrap confidence interval (CI) was estimated based on 500 bootstrap samples. Cohort 1 was used as the training set to assess the improved performance of adding TFPI and TNC-FNIII-C compared to using CA 19-9 alone. An optimal marker combination panel was developed using the forward selection method and taking into consideration the value of the AUC. The optimal cutoff for corresponding risk score was determined using the same approach as in the CLIA analysis.

Blinded Validation in Early Stage Cohorts 2 (U Pittsburgh Cohort) and 3 (EDRN Reference Set): The final selected panel and its optimal cutoff developed from cohort 1 were validated in two independent patient cohorts (cohorts 2 and 3). Because a large proportion of reference set cases in cohort 3 were free of diabetes and pancreatitis history, validation was also performed in this subcohort. Empirical ROC curves were constructed based on the panel developed from cohort 1 with corresponding AUC calculated. Also computed are sensitivity, specificity, and average sensitivity and specificity (termed "accuracy" henceforth) based on the cutoff developed from cohort 1. For estimates of AUC, sensitivity, specificity, and accuracy, 95% percentile bootstrap confidence interval were obtained based on 500 bootstrap samples. The P-values for difference in performance between the biomarker panel and the panel with CA19-9 alone were calculated based on a Z-test using bootstrap standard error estimate. All the analyses were performed using R statistical software (cran.r-project).

Further Exploratory Analysis in Cohort 3 incorporating Clinical Risk Factors: After validation of the biomarker panel (developed in cohort 1) in cohort 3, incorporation of clinical risk factors measured was further explored in cohort 3 including age and diabetes status. Logistic regression models were used to develop combinations of candidate markers (TFPI and/or TNC-FN III-C) with CA 19-9, plus age and diabetes status (not included among the subcohort free of diabetes and chronic pancreatitis) for separating each case and control group. Empirical ROC curves were constructed based on predicted risk scores with corresponding AUC calculated. For estimates of AUC, sensitivity, and specificity, 95% percentile bootstrap confidence interval were obtained based on 500 bootstrap samples, where the logistic regression model is refitted for each bootstrap sample.

Example 3—Further Validation of Migration Signature Biomarker Panel

As additional validation of the migration signature biomarker panel, ELISA assays using were conducted using the present migration signature biomarker panel and their performance was analyzed in an independent blinded plasma sample set from The International Agency for Research (IARC) consisting of 39 early-stage PDAC and 89 healthy controls. Statistical analysis was performed on the assays. For all early stage PDAC versus all healthy cohorts using the IARC set (Table 12) the combination of both biomarkers with CA19-9 significantly improved CA19-9 from an AUC 0.81 (95% CI=0.72 to 0.90) to an AUC of 0.86 (95% CI=0.78 to 0.93). When additional covariates (*Age+Sex+Center+Smoking+Drinking) were included in the analysis the combined panel further improved the AUC to 0.90 (95% CI=0.84 to 0.96). Results were significant as the algorithm utilized was distinct from that established in Example 1 and again showed that the present biomarker panel improved CA19-9 performance in multiple blinded sample sets and highlights the clinical value of the biomarker panel.

TABLE 12

Migration signature biomarker performance in IARC cohort.

| Model | AUC | P value |
|---|---|---|
| CA 19-9 | 0.81 (0.72-0.90) | <0.0001 |
| TFPI | 0.57 (0.45-0.70) | 0.2468 |
| TNC-FNIII-C | 0.71 (0.62-0.81) | <0.0001 |
| CA 19-9 + TFPI | 0.81 (0.72-0.90) | <0.0001 |
| CA 19-9 + TNC | 0.86 (0.78-0.93) | <0.0001 |

TABLE 12-continued

Migration signature biomarker performance in IARC cohort.

| Model | AUC | P value |
|---|---|---|
| CA 19-9 + TNC + TFPI | 0.86 (0.78-0.93) | <0.0001 |
| Covariates* +CA 19-9 +TFPI +TNC | 0.90 (0.84-0.96) | <0.0001 |

*Age + Sex + Center + Smoking + Drinking

TFPI levels are elevated in the plasma KC pancreatic Genetically Engineered Mouse Model (GEMM) containing Pancreatic Cancer Precursor Lesions (PanINs) versus wild type controls: One of the migration signature markers, TFPI, was screened in serum from the KC GEMM model. This GEMM model faithfully reproduces the development of pancreatic cancer in which precursor lesions, termed as PanINs, are present and can be examined at definite time points prior to the development of PDAC. The GEMM approach is based on the hypothesis that: a) genetically engineered mouse models (GEMM) of human Pancreatic ductal adenocarcinoma (PDAC) faithfully recapitulate the clinical and molecular features of human disease and, b) serial profiling of blood samples in appropriate GEMM offer the unique opportunity of developing sensitive and specific integrated biomarker panels specific for the detection of pancreatic cancer precursor lesions, PanINs. This is not possible with human samples since in human patients PanIN are predominantly detected synchronously with adenocarcinoma. It also needs to be emphasized that the GEMM models besides faithfully recapitulating the histological lesions that characterize human pancreatic tumors also display desmoplastic stroma and inflammatory responses closely resembling those observed in human patients. Thus, the goal is to identify the earliest stage at which the present biomarker panel can detect pancreatic cancer or precursor lesions that are destined to become pancreatic cancer when resection of the lesion would be assumed to be curative.

TFPI levels were examined by commercial ELISA assay in pooled plasma isolated from mice containing staged PanIN lesions (Stage 1-3) versus control wild type mice. A significant difference in TFPI levels were observed in plasma from 8 KC mice containing PanIN lesions versus 3 wild type controls (Figure). Results indicated that TFPI may be used for the early detection of precursor lesions prior to the development of pancreatic cancer.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Austin-Ward and Villaseca, Revista Medica de Chile, 126 (7):838-845, 1998.
Balasenthil et al., Cancer Prev Res. 2011;4(1):137-149.
Bukowski et al., Clinical Cancer Res., 4(10):2337-2347, 1998.
Camacho et al. J Clin Oncology 22(145): Abstract No. 2505 (antibody CP-675206), 2004.
Christodoulides et al., Microbiology, 144(Pt 11):3027-3037, 1998.
Chu et al., JOP. 2010;11:203-212.
Conlon et al., Ann Surg. 1996;223(3):273-279.
Davidson et al., J. Immunother., 21(5):389-398, 1998.
DeLong et al., Biometrics. 1988;44(3):837-845.
Haab et al., PLoS One. 2015;10(10):e0139049.
Hanibuchi et al., Int. J. Cancer, 78(4):480-485, 1998.
Hellstrand et al., Acta Oncologica, 37(4):347-353, 1998.
Hollander, Front. Immun., 3:3, 2012.
Hui and Hashimoto, Infection Immun., 66(11):5329-5336, 1998.
Hurwitz et al., Proc Natl Acad Sci USA 95(17): 10067-10071, 1998.
International Patent Publication No. WO 00/37504
International Patent Publication No. WO 01/14424
International Patent Publication No. WO 98/42752
International Patent Publication No. WO2000037504
International Patent Publication No. WO2001014424
International Patent Publication No. WO02006/121168
International Patent Publication No. WO2009/101611
International Patent Publication No. WO2009/114335
International Patent Publication No. WO2010/027827
International Patent Publication No. WO2011/066342
International Patent Publication No. WO2015016718
Ishikawa et al., Hepatogastroenterology. 1999;46(25):8-15.
Leal, M., Ann NY Acad Sci 1321, 41-54, 2014.
Mayo et al., Cancer. 2012;118(10):2674-2681.
Mokyr et al., Cancer Res 58:5301-5304, 1998.
Pardoll, Nat Rev Cancer, 12(4): 252-64, 2012
Qin et al., Proc. Natl. Acad. Sci. USA, 95(24):14411-14416, 1998.
Rahib et al., Cancer Res. 2014; 74:2913-2921.
Ryan et al., N Engl J Med. 2014; 371(22):2140-2141.
Tsuchiya et al., Ann Surg. 1986; 203(1):77-81.
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 6,207,156
U.S. Pat. No. 8,008,449
U.S. Pat. No. 8,017,114
U.S. Pat. No. 8,119,129
U.S. Pat. No. 8,354,509
U.S. Pat. No. 8,735,553
US Patent Publication No. US2010/0093557
US Patent Publication No. US2010/0190656A1
US Patent Publication No. US20110008369
US Patent Publication No. US2014022021
US Patent Publication No. US20140294898
Wu et al., Clin Adv Hemat Oncol., 11(1):53-55, 2013

What is claimed is:

1. A method for measuring the expression of the antigens TNC-FN III-C, TFPI, and CA19-9 comprising:
   (a) contacting a plurality of antigens in a sample with an anti-TNC-FN III-C antibody, an anti-TFPI antibody, and an anti-CA19-9 antibody to form antigen-antibody complexes; and
   (b) detecting the antigen-antibody complexes using detectable moieties that distinctly bind each of the antibodies, thereby measuring the expression of the antigens TNC-FN III-C, TFPI, and CA19-9, wherein an increased expression of the TNC-FN III-C, TFPI, and CA19-9 antigens as compared to a control indicates the presence of pancreatic cancer; and
   (c) administering one or more anti-cancer therapies to a subject with increased expression of the TNC-FN III-C TFPI, and CA19-9 antigens as compared to a control sample.

2. The method of claim 1, wherein the sample is obtained from a subject at risk for cancer or who has a family history of inherited cancer and/or a subject over the age of 50.

3. The method of claim 1, wherein detecting is further defined as performing an enzyme-linked immunosorbent assay (ELISA).

4. The method of claim 3, wherein the ELISA is a multiplex sandwich ELISA, wherein two or three antigens are simultaneously detected.

5. The method of claim 1, wherein the sample is diluted at least 50-fold.

6. The method of claim 1, wherein the detectable moieties comprise indocyanine green (ICG), fluorescein isothiocyanate (FITC), and/or IRDye800.

7. The method of claim 1, wherein the detectable moieties bound to the antibodies are detected by optical imaging, ultrasound, magnetic resonance imaging (MRI), positron emission tomography (PET), single-photon emission computed tomography (SPECT), or phototherapy.

8. The method of claim 3, wherein the specificity of the assay is at least 0.8.

9. The method of claim 1, wherein the control is a sample obtained from a healthy subject.

10. The method of claim 1, wherein the sample is a plasma sample, surgical or biopsy specimen, a paraffin embedded tissue, a frozen tissue imprint, peripheral blood, urine, or a fine needle aspirate.

11. The method of claim 1, wherein the pancreatic cancer is early stage pancreatic cancer, a pancreatic cancer precursor lesion (PanIN), Stage I pancreatic cancer, or Stage II pancreatic cancer.

12. The method of claim 1, wherein the one or more anti-cancer therapies are chemotherapy, radiotherapy, gene therapy, surgery, hormonal therapy, anti-angiogenic therapy, and/or immunotherapy.

13. The method of claim 1, wherein detecting comprises chemiluminescence or electron-chemiluminescence.

14. The method of claim 3, wherein the assay is a multiplex assay.

15. The method of claim 3, wherein the antibodies are biotinylated antibodies and detecting comprises adding streptavidin-conjugated fluorophores and measuring the fluorophores.

* * * * *